United States Patent
Baltezor et al.

(10) Patent No.: US 11,931,368 B2
(45) Date of Patent: Mar. 19, 2024

(54) GLUCOCORTICOID "NINTEDANIB" PARTICLES AND THEIR USE

(71) Applicant: CRITITECH, INC., Lawrence, KS (US)

(72) Inventors: Michael Baltezor, Lawrence, KS (US); Matthew McClorey, Lawrence, KS (US); Joseph S. Farthing, Lawrence, KS (US); Mark Williams, Lawrence, KS (US); Jacob Sittenauer, Lawrence, KS (US)

(73) Assignee: CRITITECH, INC., Lawrence, KS (US)

( * ) Notice: Subject to any disclaimer, the term of this patent is extended or adjusted under 35 U.S.C. 154(b) by 72 days.

(21) Appl. No.: 16/650,961

(22) PCT Filed: Sep. 28, 2018

(86) PCT No.: PCT/US2018/053366
§ 371 (c)(1),
(2) Date: Mar. 26, 2020

(87) PCT Pub. No.: WO2019/067866
PCT Pub. Date: Apr. 4, 2019

(65) Prior Publication Data
US 2020/0246355 A1    Aug. 6, 2020

Related U.S. Application Data

(60) Provisional application No. 62/730,880, filed on Sep. 13, 2018, provisional application No. 62/566,041, filed on Sep. 29, 2017.

(51) Int. Cl.
*A61K 31/569*    (2006.01)
*A61K 9/00*    (2006.01)
(Continued)

(52) U.S. Cl.
CPC .......... *A61K 31/569* (2013.01); *A61K 9/0075* (2013.01); *A61K 9/1688* (2013.01); *A61K 31/496* (2013.01); *A61P 9/00* (2018.01)

(58) Field of Classification Search
None
See application file for complete search history.

(56) References Cited

U.S. PATENT DOCUMENTS 8,586,091 B2 * 11/2013 Rimkus .............. A61K 9/2018
  544/293
9,814,685 B2    11/2017 Baltezor et al.
(Continued)

FOREIGN PATENT DOCUMENTS

| CN | 106924193 A | * | 7/2017 |
| WO | 2002/053186 | | 7/2002 |
| WO | 2010/007446 | | 1/2010 |

OTHER PUBLICATIONS

Kawashima et al. (Effect of surface morphology of carrier lactose on dry powder inhalation property of pranlukast hydrate), International Journal of Pharmaceutics, 172 179-188 (Year: 1998).*

(Continued)

*Primary Examiner* — Isis A Ghali
(74) *Attorney, Agent, or Firm* — MCDONNELL BOEHNEN HULBERT & BERGHOFF LLP

(57) ABSTRACT

Disclosed herein are particles of at least 95% by weight of a glucocorticoid that have a specific surface area of at least 10 m²/g, methods for making, such particles, and methods for their use as therapeutics. Also disclosed herein are particles of at least 95% by weight of an indolinone that have a specific surface area of at least 10 m²/g, methods for making such particles, and methods for-their use as therapeutics.

8 Claims, 28 Drawing Sheets

(51) Int. Cl.
    *A61K 9/16*        (2006.01)
    *A61K 31/496*    (2006.01)
    *A61P 9/00*        (2006.01)

(56) References Cited

U.S. PATENT DOCUMENTS

| | | |
|---|---|---|
| 9,918,957 B2 | 3/2018 | Baltezor et al. |
| 10,507,195 B2 | 12/2019 | Baltezor et al. |
| 10,729,673 B2 | 8/2020 | Baltezor et al. |
| 10,993,927 B2 | 5/2021 | Baltezor et al. |
| 11,123,322 B2 | 9/2021 | Baltezor et al. |
| 2013/0189324 A1 | 7/2013 | Monari et al. |
| 2015/0044288 A1* | 2/2015 | Surber .................... A61P 11/00 |
| | | 544/295 |
| 2018/0193259 A1* | 7/2018 | Gerhart .................. A61K 31/35 |
| 2020/0060968 A1 | 2/2020 | Surber et al. |

OTHER PUBLICATIONS

Vartiainen et al. "Development of inhalable drug formulations for idiopathic pulmonary fibrosis", Drug Delivery to the Lungs, 27, 2016 (Year: 2016).*

The International Search Report (ISR) with Written Opinion for PCT/US2018/053366 dated Jan. 16, 2019, pp. 1-19.

* cited by examiner

GLUCOCORTICOID "NINTEDANIB" PARTICLES AND THEIR USE

CROSS REFERENCE

This application is a U.S. national phase of International Application No. PCT/US2018/053366, filed on Sep. 28, 2018, which claims priority to U.S. Provisional Application No. 62/730,880, filed Sep. 13, 2018; and U.S. Provisional Application No. 62/566,041, filed Sep. 29, 2017, all of which are incorporated by reference herein in their entirety.

BACKGROUND

Dissolution rate is a key parameter in determining the rate and extent of drug absorption and bioavailability. Poor aqueous solubility and poor in vivo dissolution are limiting factors for in vivo bioavailability of many drugs. Thus, in vitro dissolution rates are recognized as an important element in drug development, and methods and compositions for increasing the dissolution rates of poorly soluble drugs are needed.

SUMMARY

In one aspect, the disclosure provides compositions, comprising particles including at least 95% by weight of a glucocorticoid, or a pharmaceutically acceptable salt thereof, wherein the particles have a specific surface area (SSA) of at least 10 $m^2/g$, or at least 11 $m^2/g$, 12.5 $m^2/g$, 14 $m^2/g$, 14.59 $m^2/g$ 17.5 $m^2/g$, 19 $m^2/g$, 20 $m^2/g$, 22.5 $m^2/g$, 25 $m^2/g$, 28 $m^2/g$, or 28.19 $m^2/g$, or have an SSA between about 10 $m^2/g$ and about 30 $m^2/g$, or between about 10 $m^2/g$ and about 28.19 $m^2/g$, or between about 10.96 $m^2/g$ and about 28.19 $m^2/g$, or between about 12.5 $m^2/g$ and about 28.19 $m^2/g$, or between about 14.59 $m^2/g$ and about 28.19 $m^2/g$, or between about 17.5 $m^2/g$ and about 28.19 $m^2/g$. In one embodiment, glucocorticoid is a methasone glucocorticoid, or a pharmaceutically acceptable salt thereof. In another embodiment, the glucocorticoid or methasone glucocorticoid is selected from the group consisting of alclometasone, beclometasone, betamethasone, clobestasol, clobetasone, clocortolone, desoximetasone, dexamethasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, halobetasol, or a pharmaceutically acceptable salt thereof. In a specific embodiment, the glucocorticoid or methasone glucocorticoid comprises fluticasone, or a pharmaceutically acceptable salt thereof, including but not limited to fluticasone furoate, fluticasone propionate, or combinations thereof. In another embodiment, the particles have a volume-mean particle size between about 0.5 µm and about 6.0 µm, between about 0.8 µm and about 5.28 µm, between about 0.89 µm and about 5.28 µm, between about 0.89 µm and about 3.0 µm, between about 0.89 µm and about 2.8 µm, or between about 2.8 µm and about 5.28 µm. In a further embodiment, the composition comprises a dosage form of glucocorticoid or methasone glucocorticoid as a dry powder for inhalation or in a suspension. In various further embodiments, the particles comprise at least 96%, 97%, 98%, 99%, or 100% of the glucocorticoid or methasone glucocorticoid. In other embodiments, the particles are uncoated, the particles include both agglomerated particles and non-agglomerated particles, and/or the composition is present as a dry powder for inhalation or in a suspension that further comprises a pharmaceutically acceptable aqueous carrier.

In another aspect the disclosure provides methods for treating a subject with a disorder that can be treated with a glucocorticoid or methasone glucocorticoid, comprising administering to a subject in need thereof an amount effective to treat the disorder of the composition of any embodiment or combination of embodiments of the glucocorticoid particles of the disclosure. In one embodiment, the glucocorticoid or methasone glucocorticoid is fluticasone or a pharmaceutically salt thereof, such as fluticasone furoate, fluticasone propionate, or combinations thereof. In another embodiment, the methods are used to treat asthma, chronic obstructive pulmonary disease (COPD), bronchitis, emphysema, rhinitis, stuffy nose, runny nose, itchy nose, sneezing, itchy eyes, and/or watery eyes. In further embodiments, the composition is administered via pulmonary administration, and/or the subject is a human subject.

In another aspect, the disclosure provides methods for making glucocorticoid compound particles of any embodiment or combination of embodiments of the disclosure, comprising:
(a) introducing (i) a solution comprising at least one solvent and a glucocorticoid into a nozzle inlet, and (ii) a compressed fluid into an inlet of a vessel defining a pressurizable chamber;
(b) passing the solution out of a nozzle orifice and into the pressurizable chamber to produce an output stream of atomized droplets, wherein the nozzle orifice is located between 5 mm and 20 mm from a sonic energy source located within the output stream, wherein the sonic energy source produces sonic energy with power output of between about 140 watts (20%) and about 560 watts (80%), and wherein the nozzle orifice has a diameter of between 50 µm and 100 µm;
(c) contacting the atomized droplets with the compressed fluid, to cause depletion of the solvent from the atomized droplets, to produce glucocorticoid particles, wherein steps (a), (b), and (c) are carried out under supercritical temperature and pressure for the compressed fluid.

In one embodiment, the methods further comprise:

(d) contacting the atomized droplets produced in step (c) with an anti-solvent to cause further depletion of the solvent from the glucocorticoid particles, wherein step (d) is carried out under supercritical temperature and pressure for the anti-solvent.

In another embodiment, the methods further comprise:

(e) receiving the plurality of glucocorticoid particles through the outlet of the pressurizable chamber; and (f) collecting the plurality of glucocorticoid particles in a collection device.

In one embodiment, the glucocorticoid is selected from the group consisting of alclometasone, beclometasone, betamethasone, clobestasol, clobetasone, clocortolone, desoximetasone, dexamethasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, halobetasol, or a pharmaceutically acceptable salt thereof. In a specific embodiment, the glucocorticoid comprises fluticasone or a pharmaceutical salt thereof, such as fluticasone furoate, fluticasone propionate, or combinations thereof. In various further embodiments, the solvent comprises acetone, and/or the compressed fluid is super critical carbon dioxide, and/or the anti-solvent is super critical carbon dioxide, and/or the method is carried out between 31.1° C. to about 60° C., and at between about 1071 psi and about 1800 psi. In one specific embodiment, the solvent is acetone, the compressed fluid is super critical carbon dioxide, and the anti-solvent is super critical carbon dioxide. In another specific embodiment, the method is carried out at between about 37.6°-38.3° C., and/or the method is carried out at between about 1100 psi and about 1300 psi. In another embodiment the nozzle orifice is located between 5 mm and 15 mm from a sonic energy source located within the output stream, wherein the sonic energy source produces sonic energy with amplitude between about 20% (140 watts) and about 80% (560 watts), or between about 30% (210 watts) and about 50% (350 watts), or between about 35% (245 watts) and about 45% (315 watts). In a further embodiment, the sonic probe operates at a frequency of between about 18 kHz and about 22 kHz. In another embodiment are disclosed glucocorticoid particles prepared by the method of any embodiment or combination of embodiments of the claims.

In another aspect, the disclosure provides compositions, comprising particles including at least 95% by weight of an indolinone, or a pharmaceutically acceptable salt thereof, wherein the particles have a specific surface area (SSA) of at least 9 $m^2/g$, or at least 9.94 $m^2/g$, 11.05 $m^2/g$, 11.79 $m^2/g$, 12.24 $m^2/g$, 12.54 $m^2/g$, 13.85 $m^2/g$, 15.6 $m^2/g$, 15.62 $m^2/g$, 20 $m^2/g$, or 20.14 $m^2/g$, or an SSA between about 9 $m^2/g$ and about 20.14 $m^2/g$, between about 9.94 $m^2/g$ and about 20.14 $m^2/g$, between about 11.05 $m^2/g$ and about 20.14 $m^2/g$, between about 11.79 $m^2/g$ and about 20.14 $m^2/g$, between about 12.24 $m^2/g$ and about 20.14 $m^2/g$, between about 12.54 $m^2/g$ and about 20.14 $m^2/g$, between about 13.85 $m^2/g$ and about 20.14 $m^2/g$, between about 15.6 $m^2/g$ and about 20.14 $m^2/g$, or between about 15.62 $m^2/g$ and about 20.14 $m^2/g$. In one embodiment, the indolinone comprises nintedanib, or a pharmaceutically acceptable salt thereof including but not limited to nintedanib esliate. In various embodiments, the particles have a volume-mean particle size between about 0.5 µm and about 5.0 µm, between about 0.99 µm and about 5 µm, between about 0.99 µm and about 4.7 µm, between about 0.99 µm and about 2.36 µm, or between about 2.36 µm and about 4.70 µm. In other embodiments, the composition comprises a dosage form of indolinone in suspension, and/or the particles comprise at least 96%, 97%, 98%, 99%, or 100% of the indolinone. In various further embodiments, the particles are uncoated and the particles include both agglomerated particles and non-agglomerated particles, and/or the composition is present as a dry powder for inhalation or in a suspension that further comprises a pharmaceutically acceptable aqueous carrier.

In another aspect the disclosure provides methods for treating a subject with a disorder that can be treated with an indolinone, comprising administering to a subject in need thereof an amount effective to treat the disorder of the indolinone particles of any embodiment or combination of embodiments disclosed herein, including but not limited to nintedanib or a pharmaceutically acceptable salt thereof, such as nintedanib esliate. In one embodiment, the methods are used to treat idiopathic pulmonary fibrosis (IPF). In various further embodiments, the composition is administered via pulmonary administration, and/or the subject is a mammalian subject, such as a human subject.

In another aspect the disclosure provides methods for making indolinone compound particles or any embodiment or combination of embodiments of the disclosure, comprising:
(a) introducing (i) a solution comprising at least one solvent and an indolinone antibiotic into a nozzle inlet, and (ii) a compressed fluid into an inlet of a vessel defining a pressurizable chamber;
(b) passing the solution out of a nozzle orifice and into the pressurizable chamber to produce an output stream of atomized droplets, wherein the nozzle orifice is located between 5 mm and 20 mm from a sonic energy source located within the output stream, wherein the sonic energy source produces sonic energy with power output of between about 140 watts (20%) and about 560 watts (80%), and wherein the nozzle orifice has a diameter of between 50 µm and 100 µm;
(c) contacting the atomized droplets with the compressed fluid, to cause depletion of the solvent from the atomized droplets, to produce indolinone particles,
wherein steps (a), (b), and (c) are carried out under supercritical temperature and pressure for the compressed fluid.

In one embodiment, the methods further comprise:
(d) contacting the atomized droplets produced in step (c) with an anti-solvent to cause further depletion of the solvent from the indolinone particles, wherein step (d) is carried out under supercritical temperature and pressure for the anti-solvent.

In another embodiment, the methods further comprise:
(e) receiving the plurality of indolinone particles through the outlet of the pressurizable chamber; and
(f) collecting the plurality of indolinone particles in a collection device.

In one specific embodiment, the indolinone comprises nintedanib, or a pharmaceutically acceptable salt thereof, including but not limited to nintedanib esliate. In various further embodiments, the solvent comprises methanol, and/or the compressed fluid is super critical carbon dioxide, and/or the anti-solvent is super critical carbon dioxide, and/or the method is carried out between 31.1° C. to about 60° C., and at between about 1071 psi and about 1800 psi. In one specific embodiment, the solvent is methanol, the compressed fluid is super critical carbon dioxide, and the anti-solvent is super critical carbon dioxide. In a further embodiment, the method is carried out at between about 37.6°-38.3° C., and/or the method is carried out at between about 1100 psi and about 1300 psi. In a further embodiment, the nozzle orifice is located between 5 mm and 15 mm from a sonic energy source located within the output stream, wherein the sonic energy source produces sonic energy with amplitude between about 20% (140 watts) and about 80% (560 watts), or between about 40% (280 watts) and about 80% (560 watts). In another embodiment, the sonic probe operates at a frequency of between about 18 kHz and about 22 kHz. In another embodiment, the disclosure provides indolinone particles prepared by the methods of any embodiment or combination of embodiments of the disclosure.

DETAILED DESCRIPTION

Figure 1A:
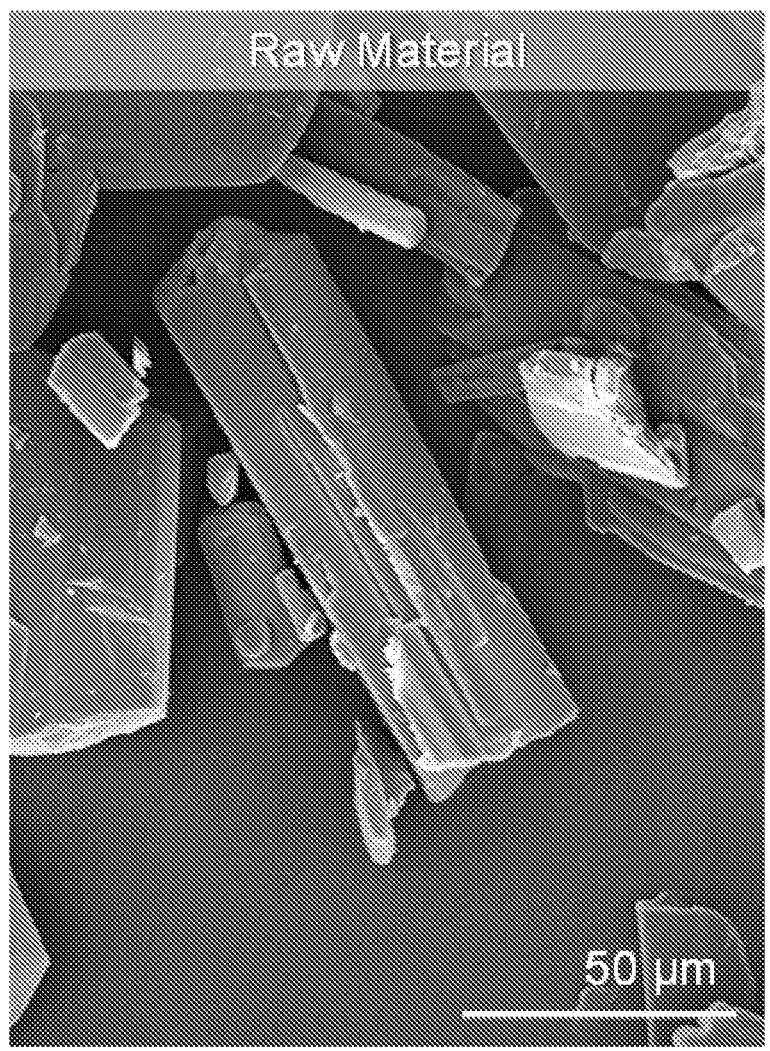
FIG. 1A is an electron micrograph of raw fluticasone particles.
Figure 1B:
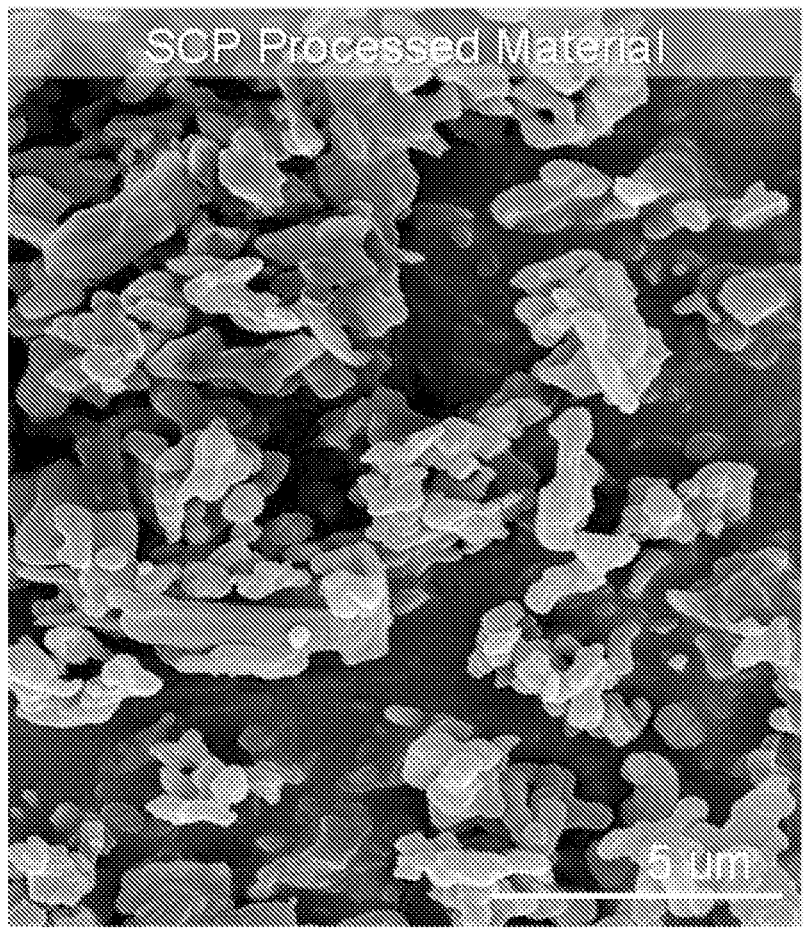
FIG. 1B is an electron micrograph of exemplary fluticasone particles of the disclosure.
Figure 2A:
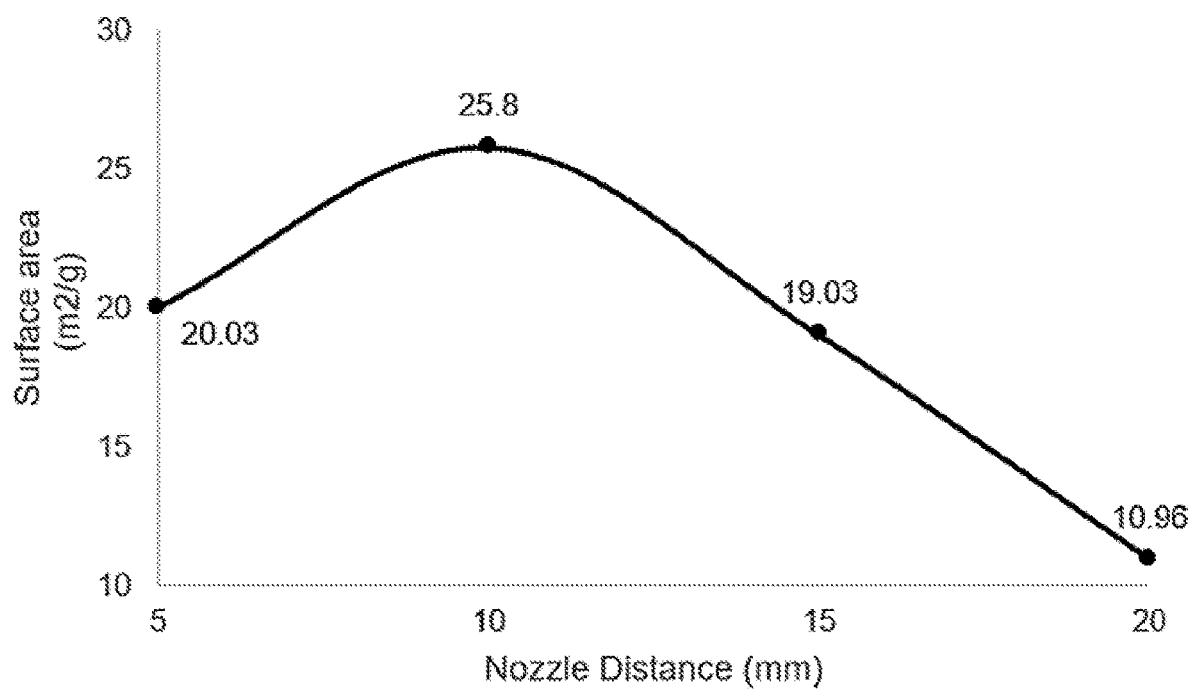
FIG. 2A is a graph of specific surface area of fluticasone particles of the disclosure as function of nozzle distance from the sonic probe during particle production.
Figure 2B:
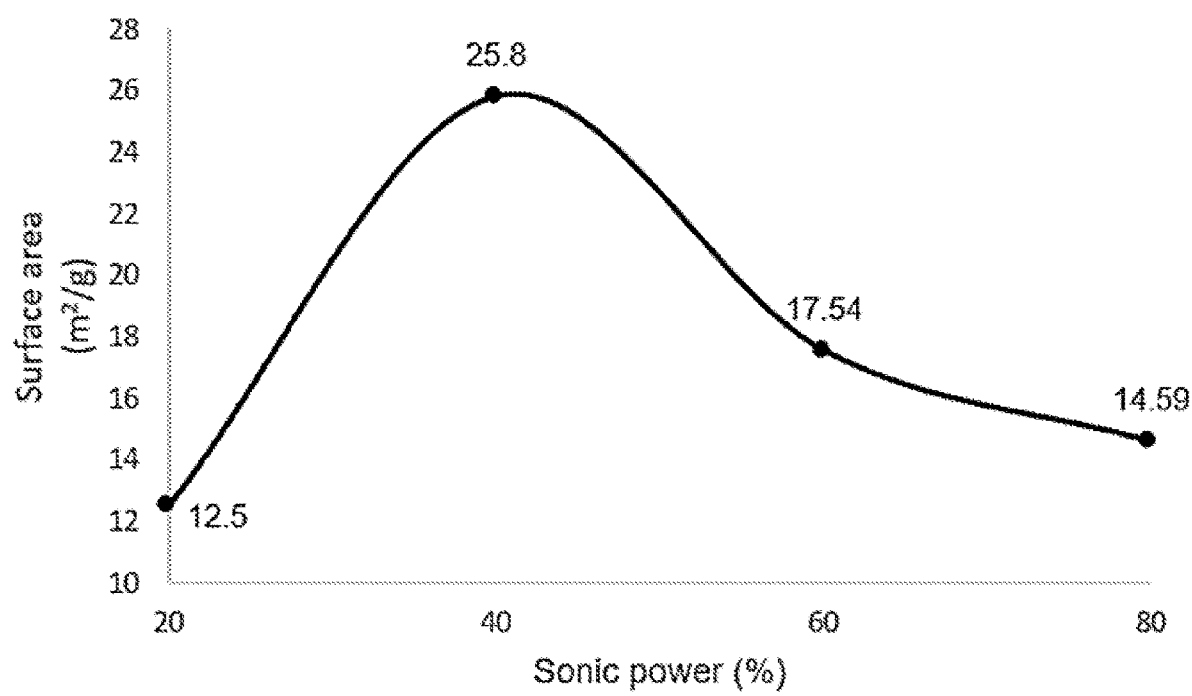
FIG. 2B is a graph of specific surface area of fluticasone particles of the disclosure as function of sonic power during particle production.
Figure 2C:
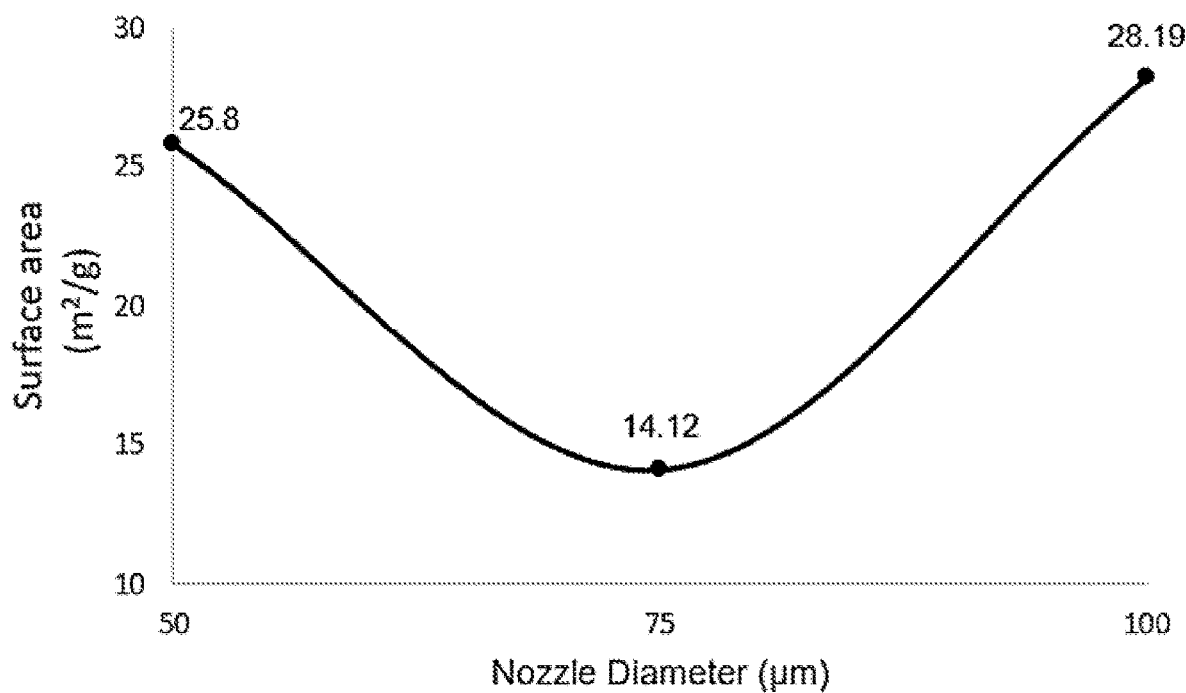
FIG. 2C is a graph of specific surface area of fluticasone particles of the disclosure as function of nozzle diameter during particle production.

As used herein, the singular forms “a”, “an” and “the” include plural referents unless the context clearly dictates otherwise. “And” as used herein is interchangeably used with “or” unless expressly stated otherwise.

As used herein, “about” means +/− five percent (5%) of the recited unit of measure.

All embodiments of any aspect of the disclosure can be used in combination, unless the context clearly dictates otherwise.

Unless the context clearly requires otherwise, throughout the description and the claims, the words ‘comprise’, ‘comprising’, and the like are to be construed in an inclusive sense as opposed to an exclusive or exhaustive sense; that is to say, in the sense of “including, but not limited to”. Words using the singular or plural number also include the plural and singular number, respectively. Additionally, the words “herein,” “above,” and “below” and words of similar import, when used in this application, shall refer to this application as a whole and not to any particular portions of the application. The compositions and methods for their use can “comprise,” “consist essentially of,” or “consist of” any of the ingredients or steps disclosed throughout the specification.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

As used herein, “about” means +/− 5% of the recited value.

In one aspect, the disclosure provides a composition, comprising particles including at least 95% by weight of a glucocorticoid, or a pharmaceutically acceptable salt thereof, wherein the particles have a specific surface area (SSA) of at least 10 $m^2$/g, or at least 11 $m^2$/g, 12.5 $m^2$/g, 14 $m^2$/g, 14.59 $m^2$/g 17.5 $m^2$/g, 19 $m^2$/g, 20 $m^2$/g, 22.5 $m^2$/g, 25 $m^2$/g, 28 $m^2$/g, or 28.19 $m^2$/g, or have an SSA between about 10 $m^2$/g and about 30 $m^2$/g, or between about 10 $m^2$/g and about 28.19 $m^2$/g, or between about 10.96 $m^2$/g and about 28.19 $m^2$/g, or between about 12.5 $m^2$/g and about 28.19 $m^2$/g, or between about 14.59 $m^2$/g and about 28.19 $m^2$/g, or between about 17.5 $m^2$/g and about 28.19 $m^2$/g.

As disclosed in the examples, the inventors have surprisingly produced glucocorticoid therapeutic particles, exemplified by fluticasone, that have significantly increased SSAs relative to raw fluticasone. The delivery and duration of action of inhaled drug particles is related to the dissolution rate of the inhaled particles and the residence time of the particles in the lung. The glucocorticoid particles of the disclosure have been demonstrated in the examples that follow to allow for enhanced delivery to the lung alveoli and to provide increased residence time in the lungs relative to currently available therapeutics. This allows for less frequent dosing and improved consistency of the amount of drug delivered, and provides a significant improvement over the art.

In various embodiments, the particles may include at least 96%, 97%, 98%, 99%, or 100% by weight of a glucocorticoid, or a pharmaceutically acceptable salt thereof.

Glucocorticoids are corticosteroids that bind to the glucocorticoid receptor (GR). In one embodiment, the glucocorticoid is a methasone glucocorticoid, or a pharmaceutically acceptable salt thereof. Methasones are defined by substitution with a methyl group at the C16α or C16β position of the pregnane steroid nucleus. In another embodiment, the glucocorticoid or methasone glucocorticoid is selected from the group consisting of:

- Alclometasone=7α-chloro-11β,17α,21-trihydroxy-16α-methylpregna-1,4-diene-3,20-dione;
- Beclometasone=9α-chloro-11β,17α,21-trihydroxy-16β-methylpregna-1,4-diene-3,20-dione;
- Betamethasone=9α-fluoro-11β,17α,21-trihydroxy-16β-methylpregna-1,4-diene-3,20-dione;
- Clobestasol=9α-fluoro-11β,17α-dihydroxy-16β-methyl-21-chloropregna-1,4-diene-3,20-dione;
- Clobetasone=9α-fluoro-16β-methyl-17α-hydroxy-21-chloropregna-1,4-diene-3,11,20-trione;
- Clocortolone=6α-fluoro-9α-chloro-11β,21-dihydroxy-16α-methylpregna-1,4-diene-3,20-dione;
- Desoximetasone=9α-fluoro-11β,21-dihydroxy-16α-methylpregna-1,4-diene-3,20-dione
- Dexamethasone=9α-fluoro-11β,17α,21-trihydroxy-16α-methylpregna-1,4-diene-3,20-dione;
- Diflorasone=6α,9α-difluoro-11β,17α,21-trihydroxy-16β-methylpregna-1,4-diene-3,20-dione;
- Difluocortolone=6α,9α-difluoro-11β,21-dihydroxy-16α-methylpregna-1,4-diene-3,20-dione;
- Fluclorolone=6α-fluoro-9α,11β-dichloro-16α,17α,21-trihydroxypregna-1,4-dien-3,20-dione;
- Flumetasone=6α,9α-difluoro-11β,17α,21-trihydroxy-16α-methylpregna-1,4-diene-3,20-dione;
- Fluocortin=6α-fluoro-11β,21-dihydroxy-16α-methyl-pregna-1,4-diene-3,20,21-trione;
- Fluocortolone=6α-fluoro-11β,21-dihydroxy-16α-methylpregna-1,4-diene-3,20-dione;
- Fluprednidene=9α-fluoro-11β,17α,21-trihydroxy-16-methylenepregna-1,4-diene-3,20-dione;
- Fluticasone=6α,9α-difluoro-11β,17α-dihydroxy-16α-methyl-21-thia-21-fluoromethylpregna-1,4-dien-3,20-dione;

Fluticasone furoate=6α,9α-difluoro-11β,17α-dihydroxy-16α-methyl-21-thia-21-fluoromethylpregna-1,4-dien-3,20-dione 17α-(2-furoate);

Halometasone=2-chloro-6α,9α-difluoro-11β,17α,21-trihydroxy-16α-methylpregna-1,4-diene-3,20-dione;

Meprednisone=16β-methyl-17α,21-dihydroxypregna-1,4-diene-3,11,20-trione;

Mometasone=9α,21-dichloro-11β,17α-dihydroxy-16α-methylpregna-1,4-diene-3,20-dione;

Mometasone furoate=9α,21-dichloro-11β,17α-dihydroxy-16α-methylpregna-1,4-diene-3,20-dione 17α-(2-furoate);

Paramethasone=6α-fluoro-11β,17α,21-trihydroxy-16α-methylpregna-1,4-diene-3,20-dione;

Prednylidene=11β,17α,21-trihydroxy-16-methylenepregna-1,4-diene-3,20-dione;

Rimexolone=11β-hydroxy-16α,17α,21-trimethylpregna-1,4-dien-3,20-dione; and

Halobetasol)=6α,9α-difluoro-11β,17α-dihydroxy-16β-methyl-21-chloropregna-1,4-diene-3,20-dione;

or a pharmaceutically acceptable salt thereof.

In one particular embodiment, the glucocorticoid or methasone glucocorticoid comprises fluticasone, or a pharmaceutically acceptable salt thereof. In specific embodiments, the fluticasone comprises fluticasone furoate, fluticasone propionate, or combinations thereof.

In these various embodiments, the glucocorticoid particles may have a volume-median particle size (Dv50) of between about 0.5 μm and about 6.0 μm, between about 0.8 μm and about 5.28 μm, between about 0.89 μm and about 5.28 μm, between about 0.89 μm and about 3.0 μm, between about 0.89 μm and about 2.8 μm, or between about 2.8 μm and about 5.28 μm.

In one embodiment, the composition comprises a dosage form of glucocorticoid as a dry powder for inhalation or in suspension (i.e.: with a pharmaceutically acceptable carrier and any other components), in a dosage deemed suitable by an attending physician for an intended use.

In embodiments where the glucocorticoid particles are aerosolized for administration, the mass median aerodynamic diameter (MMAD) of the dry powder for inhalation or the aerosol droplets of the glucocorticoid particles or suspensions thereof may be any suitable diameter for use in the disclosure. In one embodiment, the glucocorticoid particle aerosol droplets have a MMAD of between about 0.5 μm to about 6 μm diameter. In various further embodiments, the aerosol droplets have a MMAD of between about 0.5 μm to about 5.5 μm diameter, about 0.5 μm to about 5 μm diameter, about 0.5 μm to about 4.5 μm diameter, about 0.5 μm to about 4 μm diameter, about 0.5 μm to about 3.5 μm diameter, about 0.5 μm to about 3 μm diameter, about 0.5 μm to about 2.5 μm diameter, about 0.5 μm to about 2 μm diameter, about 1 μm to about 5.5 μm diameter, about 1 μm to about 5 μm diameter, about 1 μm to about 4.5 μm diameter, about 1 μm to about 4 μm diameter, about 1 μm to about 3.5 μm diameter, about 1 μm to about 3 μm diameter, about 1 μm to about 2.5 μm diameter, about 1 μm to about 2 μm diameter, about 1.5 μm to about 5.5 μm diameter, about 1.5 μm to about 5 μm diameter, about 1.5 μm to about 4.5 μm diameter, about 1.5 μm to about 4 μm diameter, about 1.5 μm to about 3.5 μm diameter, about 1.5 μm to about 3 μm diameter, about 1.5 μm to about 2.5 μm diameter, about 1.5 μm to about 2 μm diameter, about 2 μm to about 5.5 μm diameter, about 2 μm to about 5 μm diameter, about 2 μm to about 4.5 μm diameter, about 2 μm to about 4 μm diameter, about 2 μm to about 3.5 μm diameter, about 2 μm to about 3 μm diameter, and about 2 μm to about 2.5 μm diameter.

In another aspect, the disclosure provides methods for treating a subject with a disorder that can be treated with a glucocorticoid or methasone glucocorticoid, comprising administering to a subject in need thereof an amount effective to treat the disorder of the glucocorticoid particle composition of any embodiment of the disclosure described herein. In these embodiments, the glucocorticoid particles may be used, for example, to treat a disorder in the subject selected from the group consisting of asthma, chronic obstructive pulmonary disease (COPD), bronchitis, emphysema, rhinitis, stuffy nose, runny nose, itchy nose, sneezing, itchy eyes, and watery eyes. The "treating" may mean reducing symptoms of the disorder (i.e.: severity of symptoms, recurrence of symptoms, etc.), or reducing progression of the disorder. Asthma is a common long-term inflammatory disease of the airways of the lungs, and symptoms include reversible airflow obstruction, bronchospasm, episodes of wheezing, coughing, chest tightness, and shortness of breath. COPD is a type of obstructive lung disease characterized by persistent respiratory symptoms and long-term poor airflow. The main symptoms include shortness of breath and cough with sputum production. COPD is a progressive disease, meaning it typically worsens over time. Eventually everyday activities become difficult. Bronchitis is inflammation of the bronchi with symptoms including coughing up mucus, wheezing, shortness of breath, and chest discomfort. The glucocorticoid particles may be the sole therapeutic administered or may be administered with other therapeutics (such as salmeterol) as deemed appropriate by an attending physician in light of all circumstances.

In these embodiments, the glucocorticoid particle composition may be administered by any suitable route, including but not limited to orally, sublingually, by injection, or via pulmonary administration. In a specific embodiment, administration is by pulmonary administration, comprising inhalation of the glucocorticoid particles, such as by nasal, oral inhalation, or both. In this embodiment, the glucocorticoid particles may be formulated as a dry powder for inhalation or as an aerosol (i.e.: liquid droplets of a stable dispersion or suspension of the particles in a gaseous medium). Glucocorticoid particles delivered by inhalation may be deposited in the airways by gravitational sedimentation, inertial impaction, and/or diffusion. In one specific embodiment, the methods comprise inhalation of glucocorticoid particles as a dry powder or aerosolized via nebulization. In this embodiment, the inhalation results in pulmonary delivery to the subject of dry powder or aerosol droplets of the therapeutic particles or suspension thereof. In another embodiment, the methods comprise inhalation of glucocorticoid particles aerosolized via a pMDI, wherein the glucocorticoid particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the glucocorticoid particles or suspensions thereof.

The subject may be any mammal subject, including but not limited to humans and other primates, dogs, cats, horses, cattle, pigs, sheep, goats, etc.

The glucocorticoid compound particles of any embodiment or combination of embodiments can be made by a method, comprising:

(a) introducing (i) a solution comprising at least one solvent and a glucocorticoid into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 5 mm and 20 mm from a sonic energy source located within the output stream, wherein the sonic energy source produces sonic energy with power output of between about 140 watts (20%) and about 560 watts (80%), and wherein the nozzle orifice has a diameter of between 50 µm and 100 µm;

(c) contacting the atomized droplets with the compressed fluid, to cause depletion of the solvent from the atomized droplets, to produce therapeutic particles, wherein steps (a), (b), and (c) are carried out under supercritical temperature and pressure for the compressed fluid.

The method may further comprise (d) contacting the atomized droplets produced in step (c) with an anti-solvent to cause further depletion of the solvent from the glucocorticoid particles, wherein step (d) is carried out under super-critical temperature and pressure for the anti-solvent. In a further embodiment, the methods may comprise:

(e) receiving the plurality of glucocorticoid particles through the outlet of the pressurizable chamber; and (f) collecting the plurality of glucocorticoid particles in a collection device.

Any suitable solvent may be used. In non-limiting embodiments, the solvent may comprise hexafluoroisopropanol (HFIP), dimethyl sulfoxide (DMSO), acetone, ethanol, methanol, dichloromethane, ethyl acetate, chloroform, acetonitrile, and suitable combinations thereof. In a further embodiment, the solvent may comprise acetone. In one embodiment, the solute/compound is fluticasone or a pharmaceutically acceptable salt thereof, and the solvent is acetone. The glucocorticoid may make up any suitable percentage, by weight of the overall solution, depending on the specific glucocorticoid. Removal of residual solvent, such as acetone can be accomplished through extraction, either under super-critical conditions or atmospheric conditions, using a solvent in which the glucocorticoid has no solubility.

In one embodiment, the compressed fluid is super critical carbon dioxide; in another embodiment, the anti-solvent is super critical carbon dioxide. In a further embodiment, the method is carried out between 31.1° C. to about 60° C., and at between about 1071 psi and about 1800 psi. In another embodiment, the method is carried out at between about 37.6°-38.3° C. In a further embodiment, the method is carried out at between about 1100 psi and about 1300 psi. In another embodiment, the nozzle orifice is located between 5 mm and 20 mm, or 5 and 15 mm, or 10 mm from a sonic energy source located within the output stream, and the sonic energy source produces sonic energy with amplitude between about 20% (140 watts) and about 80% (560 watts), or between about 30% and about 50%, or between about 35% (245 watts) and about 45% (350 watts). In a further embodiment, the sonic probe operates at a frequency of between about 18 kHz and about 22 kHz. In various embodiments, the nozzle orifice diameter is between about 50 and about 100 µm.

In a specific embodiment, the solvent is acetone, the compressed fluid is super critical carbon dioxide; the anti-solvent is super critical carbon dioxide, the method is carried out at between about 37.6°-38.3° C. and at between about 1100 psi and about 1300 psi, and the therapeutic is fluticasone or a pharmaceutically acceptable salt thereof.

Various further embodiments are described below.

In another aspect, the disclosure provides a composition, comprising particles including at least 95% by weight of an indolinone, or a pharmaceutically acceptable salt thereof, wherein the particles have a specific surface area (SSA) of at least 9 m$^2$/g, or at least 9.94 m$^2$/g, 11.05 m$^2$/g, 11.79 m$^2$/g, 12.24 m$^2$/g, 12.54 m$^2$/g, 13.85 m$^2$/g, 15.6 m$^2$/g, 15.62 m$^2$/g, 20 m$^2$/g, or 20.14 m$^2$/g, or an SSA between about 9 m$^2$/g and about 20.14 m$^2$/g, between about 9.94 m$^2$/g and about 20.14 m$^2$/g, between about 11.05 m$^2$/g and about 20.14 m$^2$/g, between about 11.79 m$^2$/g and about 20.14 m$^2$/g, between about 12.24 m$^2$/g and about 20.14 m$^2$/g, between about 12.54 m$^2$/g and about 20.14 m$^2$/g, between about 13.85 m$^2$/g and about 20.14 m$^2$/g, between about 15.6 m$^2$/g and about 20.14 m$^2$/g, or between about 15.62 m$^2$/g and about 20.14 m$^2$/g. As disclosed in the examples, the inventors have surprisingly produced indolinone particles, exemplified by nintedanib, that have significantly increased SSAs relative to raw nintedanib.

An indolinone is either of two isomeric ketones derived from indoline, or any derivative of these compounds. In one embodiment, the indolinone comprises nintedanib, or a pharmaceutically acceptable salt thereof; an exemplary such salt thereof comprises nintedanib esliate. Nintedanib, is a medication used for the treatment of idiopathic pulmonary fibrosis (IPF) and along with other medications for some types of non-small-cell lung cancer.

In various embodiments, the particles may include at least 96%, 97%, 98%, 99%, or 100% by weight of an indolinone, or a pharmaceutically acceptable salt thereof.

In various embodiments, the indolinone particles have a volume-median particle size (Dv50) of between about 0.5 µm and about 5.0 µm, between about 0.99 µm and about 5 µm, between about 0.99 µm and about 4.7 µm, between about 0.99 µm and about 2.36 µm, or between about 2.36 µm and about 4.70 µm. In embodiments where the indolinone particles are aerosolized for administration, the mass median aerodynamic diameter (MMAD) of the dry powder or the aerosol droplets of the indolinone particles or suspensions thereof may be any suitable diameter for use in the disclosure. In one embodiment, the indolinone particle dry powder or the aerosol droplets have a MMAD of between about 0.5 µm to about 6 µm diameter. In various further embodiments, the dry powder or the aerosol droplets have a MMAD of between about 0.5 µm to about 5.5 µm diameter, about 0.5 µm to about 5 µm diameter, about 0.5 µm to about 4.5 µm diameter, about 0.5 µm to about 4 µm diameter, about 0.5 µm to about 3.5 µm diameter, about 0.5 µm to about 3 µm diameter, about 0.5 µm to about 2.5 µm diameter, about 0.5 µm to about 2 µm diameter, about 1 µm to about 5.5 µm diameter, about 1 µm to about 5 µm diameter, about 1 µm to about 4.5 µm diameter, about 1 µm to about 4 µm diameter, about 1 µm to about 3.5 µm diameter, about 1 µm to about 3 µm diameter, about 1 µm to about 2.5 µm diameter, about 1 µm to about 2 µm diameter, about 1.5 µm to about 5.5 µm diameter, about 1.5 µm to about 5 µm diameter, about 1.5 µm to about 4.5 µm diameter, about 1.5 µm to about 4 µm diameter, about 1.5 µm to about 3.5 µm diameter, about 1.5 µm to about 3 µm diameter, about 1.5 µm to about 2.5 µm diameter, about 1.5 µm to about 2 µm diameter, about 2 µm to about 5.5 µm diameter, about 2 µm to about 5 µm diameter, about 2 µm to about 4.5 µm diameter, about 2 µm to about 4 µm diameter, about 2 µm to about 3.5 µm diameter, about 2 µm to about 3 µm diameter, and about 2 µm to about 2.5 µm diameter.

In another aspect, the disclosure provides methods for treating a subject with a disorder that can be treated with an indolinone, comprising administering to a subject in need thereof an amount effective to treat the disorder of the indolinone particles of any embodiment or combination of embodiments of the disclosure. In one embodiment, the indolinone comprises nintedanib or a pharmaceutically acceptable salt thereof, such as nintedanib esliate. In one embodiment, the disorder is pulmonary fibrosis (PF), such as idiopathic PF. The methods may thus involve reducing PF symptoms, limiting the rate of increase in PF symptoms, limiting the rate of scarring of the lung tissue, etc. Symptoms of PF include a dry, non-productive cough on exertion, shortness of breath (dyspnea) with exercise, dry inspiratory bibasilar crackles on auscultation, clubbing of the digits, and abnormal pulmonary function test results, with evidence of restriction and impaired gas exchange.

The indolinone particles may be the sole therapeutic administered, or may be administered with other therapeutics as deemed appropriate by an attending physician in light of all circumstances.

In these embodiments, the indolinone particle composition may be administered by any suitable route, including but not limited to orally, sublingually, by injection or via pulmonary administration. In a specific embodiment, administration is by pulmonary administration, comprising inhalation of the indolinone particles, such as by nasal, oral inhalation, or both. In this embodiment, the indolinone particles may be formulated as a dry powder or an aerosol (i.e.: liquid droplets of a stable dispersion or suspension of the indolinone particles in a gaseous medium). Indolinone particles as a dry powder or delivered by aerosol may be deposited in the airways by gravitational sedimentation, inertial impaction, and/or diffusion. In one specific embodiment, the methods comprise inhalation of indolinone particles aerosolized via nebulization. In this embodiment, the inhalation results in pulmonary delivery to the subject of dry powder or aerosol droplets of the indolinone particles or suspension thereof. In another embodiment, the methods comprise inhalation of indolinone particles aerosolized via a pMDI, wherein the indolinone particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the indolinone particles or suspensions thereof. The subject may be any mammal subject, including but not limited to humans and other primates, dogs, cats, horses, cattle, pigs, sheep, goats, etc.

The indolinone particles of any embodiment or combination of embodiments can be made by a method, comprising
(a) introducing (i) a solution comprising at least one solvent and an indolinone antibiotic into a nozzle inlet, and (ii) a compressed fluid into an inlet of a vessel defining a pressurizable chamber;
(b) passing the solution out of a nozzle orifice and into the pressurizable chamber to produce an output stream of atomized droplets, wherein the nozzle orifice is located between 5 mm and 20 mm from a sonic energy source located within the output stream, wherein the sonic energy source produces sonic energy with power output of between about 140 watts (20%) and about 560 watts (80%), and wherein the nozzle orifice has a diameter of between 50 µm and 100 µm;
(c) contacting the atomized droplets with the compressed fluid, to cause depletion of the solvent from the atomized droplets, to produce indolinone particles, wherein steps (a), (b), and (c) are carried out under supercritical temperature and pressure for the compressed fluid.

In a further embodiment, the method may comprise (d) contacting the atomized droplets produced in step (c) with an anti-solvent to cause further depletion of the solvent from the indolinone particles, wherein step (d) is carried out under supercritical temperature and pressure for the anti-solvent. In a further embodiment, the methods may comprise:
(e) receiving the plurality of indolinone particles through the outlet of the pressurizable chamber; and
(f) collecting the plurality of indolinone particles in a collection device.

Any suitable solvent and indolinone may be used. In one non-limiting embodiment, the solvent may comprise hexafluoroisopropanol (HFIP), dimethyl sulfoxide (DMSO), acetone, ethanol, methanol, dichloromethane, ethyl acetate, chloroform, acetonitrile, and suitable combinations thereof. In a further embodiment, the solvent may comprise methanol. In one embodiment, the solute/compound is nintedanib or a pharmaceutically acceptable salt thereof, and the solvent is methanol. The quinolone antibiotic may make up any suitable percentage, by weight of the overall solution, depending on the specific quinolone antibiotic. Removal of residual solvent, such as methanol can be accomplished through extraction, either under super-critical conditions or atmospheric conditions, using a solvent in which the glucocorticoid has no solubility.

In one embodiment, the compressed fluid is super critical carbon dioxide; in another embodiment, the anti-solvent is super critical carbon dioxide. In a further embodiment, the method is carried out between 31.1° C. to about 60° C., and at between about 1071 psi and about 1800 psi. In another embodiment, the method is carried out at between about 37.6°-38.3° C. In a further embodiment, the method is carried out at between about 1100 psi and about 1300 psi. In another embodiment, the nozzle orifice is located between 5 mm and 20 mm, or between 5 mm and 15 mm from a sonic energy source located within the output stream, and the sonic energy source produces sonic energy with amplitude between about 140 watts (20%) and about 560 watts (80%), or between about 40% (280 watts) and about 80% (560 watts). In a further embodiment, the sonic probe operates at a frequency of between about 18 kHz and about 22 kHz. In various embodiments, the nozzle orifice diameter is between about 50 and about 100 µm.

In a specific embodiment, the solvent is methanol, the compressed fluid is super critical carbon dioxide; the anti-solvent is super critical carbon dioxide, the method is carried out at between about 37.6°-38.3° C. and at between about 1100 psi and about 1300 psi, and the therapeutic is nintedanib or a pharmaceutically acceptable salt thereof.

Various further embodiments are described below.

The particles of all aspects and embodiments of the disclosure comprise at least 95%, at least 96%, at least 97%, at least 98%, at least 99% or 100% therapeutic, meaning the therapeutic particles consist of or consist essentially of substantially pure therapeutic.

As used herein in all aspects, "pharmaceutically acceptable salts" of the therapeutic are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the therapeutic. The term "salts" refers to the relatively non-toxic, inorganic and organic acid addition salts of therapeutic. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

The particle size of the particles of all aspects disclosed herein can be determined by a particle size analyzer instrument and the measurement is expressed as the mean diameter based on a volume distribution (volume). A suitable particle size analyzer instrument is one which employs the analytical technique of light-light diffraction. A suitable laser-light diffraction particle size analyzer instrument is the Mastersizer, such as the Mastersizer 3000, available from Malvern Instruments, United Kingdom.

The increased specific surface area of the particles result in significant increases in dissolution rate compared to the raw compound. Dissolution takes place only at a solid/liquid interface. Therefore, increased specific surface area will increase the dissolution rate due to a larger percentage of molecules on the surface of the particle having contact with the dissolution media. Therefore, the increased specific surface area results in the significant increase in dissolution rate for the therapeutic particles compared to the raw (unprocessed) therapeutic.

In all aspects of the disclosure involving methods of treatment the subject may be any mammal, including but not limited to humans and other primates, dogs, cats, horses, cattle, pigs, sheep, goats, etc.

As used herein in all aspects of the disclosure, the terms "treatment" and "treating" means
  (i) inhibiting progression the disorder;
  (ii) inhibiting the disorder; for example, inhibiting a disorder in an individual who is experiencing or displaying the pathology or symptomatology of the disease, condition or disorder; or
  (iii) ameliorating the disorder, for example, ameliorating a disorder in an individual who is experiencing or displaying the pathology or symptomatology of the disorder (i.e., reversing or improving the pathology and/or symptomatology) such as decreasing the severity of disorder.

In one specific embodiment of all method of treatment embodiments, pulmonary administration comprises inhalation of the therapeutic particles, such as by nasal, oral inhalation, or both. In this embodiment, the therapeutic particles may be formulated as a dry powder or as an aerosol (i.e.: liquid droplets of a stable dispersion or suspension of the particles in a gaseous medium). Therapeutic particles delivered by aerosol may be deposited in the airways by gravitational sedimentation, inertial impaction, and/or diffusion. Any suitable device for generating the aerosol may be used, including but not limited to pressured meter inhalers (pMDI), nebulizers, dry powder inhalers (DPI), and soft-mist inhalers.

In one specific embodiment of all embodiments, the methods comprise inhalation of therapeutic particles as dry powders or aerosolized via nebulization. Nebulizers generally use compressed air or ultrasonic power to create inhalable aerosol droplets of the particles or suspensions thereof. In this embodiment, the inhalation results in pulmonary delivery to the subject of dry powder or aerosol droplets of the therapeutic particles or suspension thereof.

In another embodiment of all embodiments, the methods comprise inhalation of therapeutic particles aerosolized via a pMDI, wherein the therapeutic particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the therapeutic particles or suspensions thereof.

In embodiments of all embodiments where the therapeutic particles are aerosolized for administration, the mass median aerodynamic diameter (MMAD) of the dry powder or aerosol droplets of the therapeutic particles or suspensions thereof may be any suitable diameter for use in the disclosure. In one embodiment, the dry powder or aerosol droplets have a MMAD of between about 0.5 µm to about 6 µm diameter. In various further embodiments, the dry powder or aerosol droplets have a MMAD of between about 0.5 µm to about 5.5 µm diameter, about 0.5 µm to about 5 µm diameter, about 0.5 µm to about 4.5 µm diameter, about 0.5 µm to about 4 µm diameter, about 0.5 µm to about 3.5 µm diameter, about 0.5 µm to about 3 µm diameter, about 0.5 µm to about 2.5 µm diameter, about 0.5 µm to about 2 µm diameter, about 1 µm to about 5.5 µm diameter, about 1 µm to about 5 µm diameter, about 1 µm to about 4.5 µm diameter, about 1 µm to about 4 µm diameter, about 1 µm to about 3.5 µm diameter, about 1 µm to about 3 µm diameter, about 1 µm to about 2.5 µm diameter, about 1 µm to about 2 µm diameter, about 1.5 µm to about 5.5 µm diameter, about 1.5 µm to about 5 µm diameter, about 1.5 µm to about 4.5 µm diameter, about 1.5 µm to about 4 µm diameter, about 1.5 µm to about 3.5 µm diameter, about 1.5 µm to about 3 µm diameter, about 1.5 µm to about 2.5 µm diameter, about 1.5 µm to about 2 µm diameter, about 2 µm to about 5.5 µm diameter, about 2 µm to about 5 µm diameter, about 2 µm to about 4.5 µm diameter, about 2 µm to about 4 µm diameter, about 2 µm to about 3.5 µm diameter, about 2 µm to about 3 µm diameter, and about 2 µm to about 2.5 µm diameter. A suitable instrument for measuring the mass median aerodynamic diameter (MMAD) and geometric standard deviation (GSD) of the dry powder or aerosol droplets is a seven-stage aerosol sampler such as the Mercer-Style Cascade Impactor.

In embodiments of all aspects of the disclosure where the therapeutic particles are administered, the therapeutic particles may have a mean aerodynamic particle size (MMAD) of between 1 µm and 5 µm and be administered as a dry powder. In this embodiment, the therapeutic particle can consist of the therapeutic particle or the therapeutic particle blended with a carrier particle such as lactose for pulmonary delivery The "amount effective" of the therapeutic particle of all aspects of the disclosure can be determined by an attending physician based on all relevant factors. The therapeutic particles may be the sole therapeutic administered, or may be administered with other therapeutics as deemed appropriate by an attending physician in light of all circumstances.

In various embodiments, the therapeutic particles of all aspects of the disclosure are made by modified versions of "precipitation with compressed anti-solvents" (PCA) methods as disclosed in international patent application publications WO 2016/197091, WO 2016/197100, and WO 2016/

197101; all of which are herein incorporated by reference. This PCA process may also be known as "supercritical precipitation" (SCP).

In PCA particle size reduction methods using supercritical carbon dioxide, supercritical carbon dioxide (anti-solvent) and appropriate solvent are employed to generate uncoated therapeutic particles as small as 0.1 to 5 microns within a well-characterized particle-size distribution. The carbon dioxide and solvent are removed during processing (up to 0.5% residual solvent may remain), leaving therapeutic particles as a powder.

As used herein, the "specific surface area" (SSA) is the total surface area of the particle per unit of compound mass as measured by the Brunauer-Emmett-Teller ("BET") isotherm by the following method: a known mass between 200 and 300 mg of the analyte is added to a 30 mL sample tube. The loaded tube is then mounted to a Porous Materials Inc. SORPTOMETER®, model BET-202A. The automated test is then carried out using the BETWIN® software package and the surface area of each sample is subsequently calculated. Such an increase in SSA results in significant increases in dissolution rates in relevant media as compared to therapeutic particles produced by conventional means.

The "therapeutic particles" can include both agglomerated therapeutic particles and non-agglomerated therapeutic particles; since the SSA is determined on a per gram basis it takes into account both agglomerated and non-agglomerated therapeutic particles in the composition. The BET specific surface area test procedure is a compendial method included in both the United States Pharmaceopeia and the European Pharmaceopeia.

In various embodiments of all aspects disclosed herein, the particles are uncoated (neat) individual particles; the particles are not bound to or conjugated to any substance; no substances are absorbed or adsorbed onto the surface of the particles; the particles are not encapsulated in any substance; the particles are not coated with any substance; the particles are not microemulsions, nanoemulsions, microspheres, or liposomes of a compound; and/or the particles are not bound to, attached to, encapsulated in, or coated with a monomer, a polymer (or biocompatible polymer), a protein, a surfactant, or albumin. In some embodiments, a monomer, a polymer (or biocompatible polymer), a copolymer, a protein, a surfactant, or albumin is not absorbed or adsorbed onto the surface of the particles. In some embodiments, the compositions are free of/do not include or contain a polymer/copolymer or biocompatible polymer/copolymer. In some embodiments, the compositions are free of/do not include or contain a protein. In some aspects of the disclosure, the compositions are free of/do not include or contain albumin. In some aspects of the disclosure, the compositions are free of/do not include or contain hyaluronic acid. In some aspects of the disclosure, the compositions are free of/do not include or contain a conjugate of hyaluronic acid and a therapeutic. In some aspects of the disclosure, the compositions are free of/do not include or contain a conjugate of hyaluronic acid and therapeutic. In some aspects of the disclosure, the compositions are free of/do not include or contain poloxamers, polyanions, polycations, modified polyanions, modified polycations, chitosan, chitosan derivatives, metal ions, nanovectors, poly-gamma-glutamic acid (PGA), polyacrylic acid (PAA), alginic acid (ALG), Vitamin E-TPGS, dimethyl isosorbide (DMI), methoxy PEG 350, citric acid, anti-VEGF antibody, ethylcellulose, polystyrene, polyanhydrides, polyhydroxy acids, polyphosphazenes, polyorthoesters, polyesters, polyamides, polysaccharides, polyproteins, styrene-isobutylene-styrene (SIBS), a polyanhydride copolymer, polycaprolactone, polyethylene glycol (PEG), Poly (bis(P-carboxyphenoxy)propane-sebacic acid, poly(d,l-lactic acid) (PLA), poly(d.l-lactic acid-co-glycolic acid) (PLAGA), and/or poly(D, L lactic-co-glycolic acid (PLGA). In some embodiments, the particles are in crystalline form. In other embodiments, the particles are in amorphous form, or a combination of both crystalline and amorphous form.

In one embodiment of all aspects of the present disclosure, the therapeutic particles for administration comprises a dosage form of therapeutic as a dry powder or in suspension (i.e.: with a pharmaceutically acceptable carrier, and or in an aerosol formulation) of between about 0.1 mg/ml and about 100 mg/ml therapeutic. In various further embodiments, the dosage form may be between about 0.5 mg/ml and about 100 mg/ml, about 1 mg/ml and about 100 mg/ml, about 2 mg/ml and about 100 mg/ml, about 5 mg/ml and about 100 mg/ml, about 10 mg/ml and about 100 mg/ml, about 25 mg/ml and about 100 mg/ml, about 0.1 mg/ml and about 75 mg/ml, about 0.5 mg/ml and about 75 mg/ml, about 1 mg/ml and about 75 mg/ml, about 2 mg/ml and about 75 mg/ml, about 5 mg/ml and about 75 mg/ml, about 10 mg/ml and about 75 mg/ml, about 25 mg/ml and about 75 mg/m, about 0.1 mg/ml and about 50 mg/ml, about 0.5 mg/ml and about 50 mg/ml, about 1 mg/ml and about 50 mg/ml, about 2 mg/ml and about 50 mg/ml, about 5 mg/ml and about 50 mg/ml, about 10 mg/ml and about 50 mg/ml, about 25 mg/ml and about 50 mg/m, about 0.1 mg/ml and about 25 mg/ml, about 0.5 mg/ml and about 25 mg/ml, about 1 mg/ml and about 40 mg/ml, about 1 mg/ml and about 25 mg/ml, about 2 mg/ml and about 25 mg/ml, about 5 mg/ml and about 25 mg/ml, about 10 mg/ml and about 25 mg/ml, about 0.1 mg/ml and about 15 mg/ml, about 0.5 mg/ml and about 15 mg/ml, about 1 mg/ml and about 15 mg/ml, about 2 mg/ml and about 15 mg/ml, about 5 mg/ml and about 15 mg/ml, about 10 mg/ml and about 15 mg/ml, about 0.1 mg/ml and about 10 mg/ml, about 0.5 mg/ml and about 10 mg/ml, about 1 mg/ml and about 10 mg/ml, about 2 mg/ml and about 10 mg/ml, about 5 mg/ml and about 10 mg/ml, about 0.1 mg/ml and about 5 mg/ml, about 0.5 mg/ml and about 5 mg/ml, about 1 mg/ml and about 5 mg/ml, about 2 mg/ml and about 5 mg/ml, about 0.1 mg/ml and about 2 mg/ml, about 0.5 mg/ml and about 2 mg/ml, about 1 mg/ml and about 2 mg/ml, about 0.1 mg/ml and about 1 mg/ml, about 0.5 mg/ml and about 1 mg/ml, about 0.1 mg/ml and about 0.5 mg/ml, about 0.1 mg/ml and about 15 mg/ml, about 0.5 mg/ml and about 15 mg/ml, about 1 mg/ml and about 15 mg/ml, about 2 mg/ml and about 15 mg/ml, about 5 mg/ml and about 15 mg/ml, about 3 mg/ml and about 8 mg/ml, or about 4 mg/ml and about 6 mg/ml therapeutic, or at least about 0.1, 0.5, 1, 10, 20, 25, 50, 75, or 100 mg/ml therapeutic.

In one embodiment of all aspects of the present disclosure, the particles are present in a liquid carrier, for example, prior to aerosolization. Any suitable liquid carrier may be used, such as an aqueous liquid carrier. Any suitable aqueous liquid carrier can be used, including but not limited to 0.9% saline solution (normal saline) such as 0.9% Sodium Chloride for Injection USP. In another embodiment of all aspects of the present disclosure, the particles are present in a suspension, for example, prior to aerosolization. In some embodiments, the suspension includes an aqueous carrier. The carrier can comprise buffering agent, osmotic salt and/or surfactant in water, and other agents for adjustment of pH, isotonicity and viscosity. In one embodiment employing an aqueous carrier, the concentration of surfactant is less than 1% on a w/w or w/v basis; in other embodiments, less than 0.5%, less than 0.25%, or about 0.1%. In some embodiments, the composition or suspension excludes polymers, proteins (such as albumin), polyethoxylated castor oil, and/or polyethylene glycol glycerides composed of mono-, di- and triglycerides and mono- and diesters of polyethylene glycol.

In some embodiments of all aspects of the present disclosure, the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise particles, water, buffer and salt. It optionally further comprises a surfactant. In some embodiments, the suspension consists essentially of or consists of water, particles suspended in the water and buffer. The suspension can further contain an osmotic salt.

In all aspects of the disclosure involving methods for producing therapeutic particles, the methods of the disclosure utilize a sonic energy source located directly in the output stream of the therapeutic dissolved in the solvent, as disclosed in US published patent application number 20160354336, incorporated by reference herein it its entirety. Any suitable source of sonic energy may be used that is compatible with the methods of the disclosure, including but not limited to sonic horn, a sonic probe, or a sonic plate. In various embodiments, the nozzle orifice is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 mm, about 8 mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm, about 16 mm and about 20 mm, about 16 mm and about 18 mm, about 18 mm and about 20 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm from the sonic energy source.

Any suitable source of sonic energy may be used that is compatible with the methods of the making the therapeutic particles of any aspect of the disclosure, including but not limited to sonic horn, a sonic probe, or a sonic plate. In various further embodiments, the sonic energy source produces sonic energy with a power output between about 7 watts and about 700 watts. In light of the teachings herein, one of skill in the art can determine an appropriate sonic energy source having a specific total power output to be used. In one embodiment, the sonic energy source has a total power output of between about 500 and about 900 watts; in various further embodiments, between about 600 and about 800 watts, about 650-750 watts, or about 700 watts.

The power output may also be expressed in terms of percent sonic power, with a conversion to watts as shown below in Table 1.

TABLE 1

| Percent | Watts |
|---|---|
| 100.00% | 700 |
| 80.00% | 560 |
| 60.00% | 420 |
| 40.00% | 280 |
| 20.00% | 140 |

In various further embodiments all aspects of the disclosure involving methods for producing therapeutic particles, the sonic energy source produces sonic energy with a power output between about 7 and about 700 watts, 35 and about 700 watts, about 70 and about 700 watts, 140 and about 700 watts, about 210 and about 700 watts, about 280 and about 700 watts, about 350 and about 700 watts, about 420 and about 700 watts, about 490 and about 700 watts, about 560 and about 700 watts, about 630 and about 700 watts, about 7 and about 630 watts, about 35 and about 630 watts, about 70 and about 630 watts, about 140 and about 630 watts, about 210 and about 630 watts, about 280 and about 630 watts, about 350 and about 630 watts, about 420 and about 630 watts, about 490 and about 630 watts, about 560 and about 630 watts, about 7 and about 560 watts, about 35 and about 560 watts, about 70 and about 560 watts, about 140 and about 560 watts, about 210 and about 560 watts, about 280 and about 560 watts, about 360 and about 560 watts, about 420 and about 560 watts, about 490 and about 560 watts, about 7 and about 490 watts, about 35 and about 490 watts, about 70 and about 490 watts, about 140 and about 490 watts, about 210 and about 490 watts, about 280 and about 490 watts, about 350 and about 490 watts, about 420 and about 490 watts, about 7 and about 420 watts, about 35 and about 420 watts, about 70 and about 420 watts, about 140 and about 420 watts, about 210 and about 420 watts, about 280 and about 420 watts, about 350 and about 420 watts, about 7 and about 350 watts, about 35 and about 350 watts, about 70 and about 350 watts, about 140 and about 350 watts, about 210 and about 350 watts, about 280 and about 350 watts, about 7 and about 280 watts, about 35 and about 280 watts, about 70 and about 280 watts, about 140 and about 280 watts, about 210 and about 280 watts, about 7 and about 210 watts, about 35 and about 210 watts, about 70 and about 210 watts, about MO and about 210 watts, about 7 and about 140 watts, about 35 and about 140 watts, about 70 and about 140 watts, about 7, 35, 70, 140, 210, 280, 350, 420, 490, 560, 630, or about 700 watts. In various embodiments, the sonic energy source produces sonic energy with power output of about 1%-80%, 20-80%, 30-70%, 40-60%, or about 60% of the total power that can be generated using the sonic energy source. In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or a frequency of about 20 kHz on the sonic energy source is utilized.

In various further embodiments all aspects of the disclosure involving methods for producing therapeutic particles, the nozzle orifice has a diameter of between about 20 µm and about 125 µm, about 20 µm and about 115 µm, about 20 µm and about 100 µm, about 20 µm and about 90 µm, about 20 µm and about 80 µm, about 20 µm and about 70 µm, about 20 µm and about 60 µm, about 20 µm and about 50 µm, about 20 µm and about 40 µm, about 20 µm and about 30 µm, between about 30 µm and about 125 µm, about 30 µm and about 115 µm, about 30 µm and about 100 µm, about 30 µm and about 90 µm, about 30 µm and about 80 µm, about 30 µm and about 70 µm, about 30 µm and about 60 µm, about 30 µm and about 50 µm, about 30 µm and about 40 µm, between about 40 µm and about 125 µm, about 40 µm and about 115 µm, about 40 µm and about 100 µm, about 40 µm and about 90 µm, about 40 µm and about 80 µm, about 40 µm and about 70 µm, about 40 µm and about 60 µm, about 40 µm and about 50 µm, between about 50 µm and about 125 µm, about 50 µm and about 115 µm, about 50 µm and about 100 µm, about 50 µm and about 90 µm, about 50 µm and about about 50 µm and about 70 µm, about 50 µm and about 60 µm, between about 60 µm and about 125 µm, about 60 µm and about 115 µm, about 60 µm and about 100 µm, about 60 µm and about 90 µm, about 60 µm and about 80 µm, about 60 µm and about 70 µm, between about 70 µm and about 125 µm, about 70 µm and about 115 µm, about 70 µm and about 100 µm, about 70 µm and about 90 µm, about 70 µm and about 80 µm, between about 80 µm and about 125 µm, about 80 µm and about 115 µm, about 80 µm and about 100 µm, about 80 µm and about 90 µm, between about 90 µm and about 125 µm, about 90 µm and about 115 µm, about 90 µm and about 100 µm, between about 100 µm and about 125 µm, about 100 µm and about 115 µm, between about 115 µm and about 125 µm, about 20 µm, 30 µm, 40 µm, 50 µm, 60 µm, 70 µm, 80 µm, 90 µm, 100 µm, 115 µm, or about 120 µm. The nozzle is inert to both the solvent and the compressed fluid used in the methods.

In another embodiment all aspects of the disclosure involving methods for producing therapeutic particles, the nozzle may include an outlet aperture that may comprise include a plurality of ridges to create a vortex within the nozzle such that the solvent exits the nozzle via turbulent flow. In one embodiment, the nozzle may include a porous fit interior to the nozzle such that the solvent exits the nozzle via turbulent flow. In another embodiment, the outlet aperture of the nozzle may have a small diameter such that the solvent exits the nozzle via turbulent flow. These various embodiments that cause turbulent flow may assist in mixing the solvent with the anti-solvent within the pressurizable chamber. Further, the inlet tube of the nozzle may have an inner diameter with a range from about 1.5875 mm to about 6.35 mm.

In further examples all aspects of the disclosure involving methods for producing therapeutic particles, the system may include a plurality of nozzles, with each nozzle positioned at a different angle between a longitudinal axis of the vessel and a longitudinal axis of the nozzle and/or a different distance between the nozzle orifice and the sonic energy source. A given nozzle of the plurality of nozzles may be chosen for a given production run to produce a certain type of therapeutic particle having a given SSA.

The compressed fluid for use in all aspects of the disclosure involving methods for producing therapeutic particles is capable of forming a supercritical fluid under the conditions used, and the therapeutic that forms the particles is poorly soluble or insoluble in the compressed fluid. As is known to those of skill in the art, a supercritical fluid is any substance at a temperature and pressure above its critical point, where distinct liquid and gas phases do not exist. Steps (a), (b), and (c) of the methods for making particles of the disclosure are carried out under supercritical temperature and pressure for the compressed fluid, such that the compressed fluid is present as a supercritical fluid during these processing steps.

The compressed fluid can serve as a solvent for and can be used to remove unwanted components in the particles. Any suitable compressed fluid may be used in the methods of the disclosure; exemplary such compressed fluids are disclosed in U.S. Pat. Nos. 5,833,891 and 5,874,029. In one non-limiting embodiment, suitable supercritical fluid-forming compressed fluids and/or anti-solvents can comprise carbon dioxide, ethane, propane, butane, isobutane, nitrous oxide, xenon, sulfur hexafluoride and trifluoromethane. The anti-solvent recited in step (d) to cause further solvent depletion, is a compressed fluid as defined above, and may be the same compressed fluid used in steps (a-c), or may be different. In one embodiment, the anti-solvent used in step (d) is the same as the compressed fluid used in steps (a-c). In a preferred embodiment, the compressed fluid and the anti-solvent are both super-critical carbon dioxide.

In all cases, the compressed fluid and anti-solvent should be substantially miscible with the solvent while the therapeutic should be substantially insoluble in the compressed fluid, i.e., the therapeutic, at the selected solvent/compressed fluid contacting conditions, should be no more than about 10% by weight soluble in the compressed fluid or anti-solvent, and preferably no more than 9%, 8%, 7%, 6%, 5%, 4%, 3%, 2%, 1%, 0.5%, soluble, or essentially completely insoluble. In one preferred embodiment, the compressed fluid and the anti-solvent are the same.

The supercritical conditions used in the methods for making therapeutic particles of all aspects of the disclosure are typically in the range of from 1× to about 1.4×, or 1× to about 1.2× of the critical temperature of the supercritical fluid (so long as the therapeutic is thermally stable at the elevated temperature), and from 1× to about 7×, or 1× to about 2×, of the of the supercritical pressure for the compressed fluid. It is well within the level of those of skill in the art to determine the critical temperature and pressure for a given compressed fluid or anti-solvent. In one embodiment, the compressed fluid and anti-solvent are both super critical carbon dioxide, and the critical temperature is at least 31.1° C. and up to about 60° C., and the critical pressure is at least 1071 psi and up to about 1800 psi or higher (i.e.: no theoretical upper limit, so long as the processing equipment can sustain the higher psi). In another embodiment, the compressed fluid and anti-solvent are both super critical carbon dioxide, and the critical temperature is at least 35° C. and up to about 55° C. or higher (i.e.: no theoretical upper limit, so long as the processing equipment can sustain the higher temperature), and the critical pressure is at least 1070 psi and up to about 1500 psi. It will be understood by those of skill in the art that the specific critical temperature and pressure may be different at different steps during the processing. For example, $CO_2$ is super critical at all pressures greater than 1071 psi if the temperature is above 31.1° C.

Any suitable pressurizable chamber may be used, including but not limited to those disclosed in U.S. Pat. Nos. 5,833,891 and 5,874,029. Similarly, the steps of contacting the atomized droplets with the compressed fluid to cause depletion of the solvent from the droplets; and contacting the droplets with an anti-solvent to cause further depletion of the solvent from the droplets, to produce therapeutic particles can be carried out under any suitable conditions, including but not limited to those disclosed in U.S. Pat. Nos. 5,833,891 and 5,874,029.

The flow rate can be adjusted as high as possible to optimize output but below the pressure limitations for the equipment, including the nozzle orifice. In one embodiment, the flow rate of the solution through the nozzle has a range from about 0.5 mL/min to about 30 mL/min. In various further embodiments, the flow rate is between about 0.5 mL/min to about 25 mL/min, 0.5 mL/min to about 20 mL/min, 0.5 mL/min to about 15 mL/min, 0.5 mL/min to about 10 mL/min, 0.5 mL/min to about 4.5 mL/min, about 1 mL/min to about 30 mL/min, about 1 mL/min to about 25 mL/min, about 1 mL/min to about 20 mL/min, 1 mL/min to about 15 mL/min, about 1 mL/min to about 10 mL/min, about 2 mL/min to about 30 mL/min, about 2 mL/min to about 25 mL/min, about 2 mL/min to about 20 mL/min, about 2 mL/min to about 15 mL/min, or about 2 mL/min to about 10 mL/min. The solution of therapeutic subject to the flow rate can be any suitable concentration, such as between about 1 mg/ml and about 80 mg/ml.

In one embodiment, the methods further comprise receiving the plurality of particles through the outlet of the pressurizable chamber; and collecting the plurality of particles in a collection device.

In another aspect, the disclosure provides therapeutic particles prepared by the method of any embodiment or combination of embodiments of the methods of making therapeutic particles of the disclosure.

Examples

1. Production of Fluticasone Particles Using SCP

A drug solution of fluticasone propionate in acetone having a concentration of 30 mg/mL was prepared. A Lennox nozzle with variable diameters (50 μm, 75 μm, or 100 μm) and a sonic probe (Qsonica, model number Q700) were positioned in the crystallization chamber approximately 5 mm, 10 mm, 15 mm, or 20 mm apart. A stainless steel mesh filter with approximately 20 nm holes was attached to the crystallization chamber to collect the precipitated fluticasone nanoparticles. The supercritical carbon dioxide was placed in the crystallization chamber of the manufacturing equipment and brought to approximately 1200 psi at about 38° C. and a flow rate of 65 standard liter per minute (slpm). The sonic probe was adjusted to 20% (140 watts), 40% (280 watts), 60% (420 watts), or 80% (560 watts) of total output power at a frequency of 20 kHz. The acetone solution containing the fluticasone was pumped through the nozzle at a flow rate of 2 mL/minute for approximately 8 min. Drug crystallization occurred in the vessel and during this period the system pressure, temperature, and flow rate were kept constant. Once the desired amount of drug solution has been introduced into the system, the solution inlet valve was closed and pure solvent (3-5 mL) was introduced through the nozzle in order to rinse the nozzle. $CO_2$ was continually pumped through the system for about 30 minutes to flush all remaining solvent and dry the system. The sonication was then stopped, and the drug particles were collected from the system vessel and oven dried for 20 hours to remove all residual solvent.

Fluticasone nanoparticles produced had the physical characteristics shown in Table 2A, and representative images of the processed fluticasone are shown in FIG. 1B:

TABLE 2A

| Characteristic | Raw | SCP | % Change |
|---|---|---|---|
| Dv10 μm | 10.9 | 0.89 | −92% |
| Dv50 μm | 39.0 | 2.80 | −93% |
| Dv90 μm | 74.4 | 5.28 | −93% |
| SSA ($m^2/g$) | 4.11 | 10.96-28.19 | +586% |

FIGS. 2A-2C are graphs showing the effect on specific surface are of the particles based on nozzle distance from the sonic probe, sonic power, and nozzle diameter, respectively.

2. Pharmacokinetic Rat Study for Processed Fluticasone Particles

In short, male Charles River Sprague Dawley (CD) Rats, 7-8 weeks old and weighing approximately 150-450 g were used for the study. Prior to the first exposure, animals deemed healthy for the study and acclimated to nose-only exposure tubes were weighed and randomly assigned to study groups by weight stratification. Fluticasone propionate powder was administered by nose-only inhalation for 30 minutes. The target dose was 3 mg/kg. The Dv50 for the fluticasone particles was between 3.16 and 3.61 for different batches used. The specific surface area of the fluticasone propionate particles used in this study was approximately between 13.0 and 17.5 $m^2/g$ (three different lots of SCP processed fluticasone propionate with specific surface areas of 17.3, 17.5 and 13.0 $m^2/g$ were used in the study; see Table 2B).

TABLE 2B

| Physical characteristics of particles used in the rat study | | | |
|---|---|---|---|
| | Lot 1 | Lot 2 | Lot 3 |
| Dv10 | 0.976 | 1.09 | 1.09 |
| Dv50 | 3.16 | 3.21 | 3.61 |
| Dv90 | 7.05 | 6.86 | 8.08 |
| SAA | 17.3 | 17.5 | 13.0 |

For the inhalation, the inhalation exposure system was used. The inhalation exposure chamber consists of a rotating brush generator (RBG) (Palas GmbH, Germany) and an exposure chamber with RBG outlet discharging either vertically or horizontally into the exposure chamber. The test drug was packed into a piston. Feed rate was adjusted to achieve the target aerosol concentration. Nose-only exposure tubes were connected directly to the ports on the exposure chamber, and chamber oxygen levels (%) were monitored throughout the exposure. To monitor the concentration of the drug (1, 2, 4, 6, 12, 24, 48 hours post dosing; 3 animals per time point), the exposure atmospheres were sampled directly from one of the exposure ports onto membrane filters (47-mm GF/A filters, GE Whatman, Pittsburgh, PA) at a nominal flow rate through a separate sample line. The concentration was monitored both gravimetrically (e.g., by weighing the filter) and chemically (e.g., by using a high performance liquid chromatography (HPLC)). For the tail vein injections, alert rats were restrained in modified nose-only tubes for lateral tail vein injection. Drug volume was adjusted based on body weight.

Respiratory minute volume (RMV; liters per min) was calculated using the following allometric equation: $RMV=0.608BW^{0.852}$, where BW is the exposure day body weight in kilograms (Alexander et al. *Inhalation Toxicology;* 20 (13): 1179-89. 2008). The estimated dose was calculated using the following formula: Dose=(C×RMV×T×DF)/BW, where C is the average concentration of the test article in the exposure atmosphere, T (min) is exposure time, and the deposition fraction (DF) is assumed to be 10%. Individual animal dose was calculated, and the group average was then estimated.

Animals were examined twice per day (morning and afternoon). At scheduled PK time points or in case of moribund euthanasia, animals were euthanized by intraperitoneal injection of an overdose of a barbiturate-based sedative. After euthanasia, examination was performed on all animals and consisted of a complete external and internal examination including body orifices (ears, nostrils, mouth, anus, etc.) and cranial, thoracic, and abdominal organs and tissues. Blood samples (≤4 mL) were then collected into K2EDTA tubes, centrifuged at 1300 g for 10 min at 2-8° C., and plasma analyzed by HPLC. A ±5 min window was allowed for the blood collections. For each animal except those found dead, left and right lungs were grossly examined, weighed separately, and lung tissue sample analyzed by HPLC.

Figure 5:
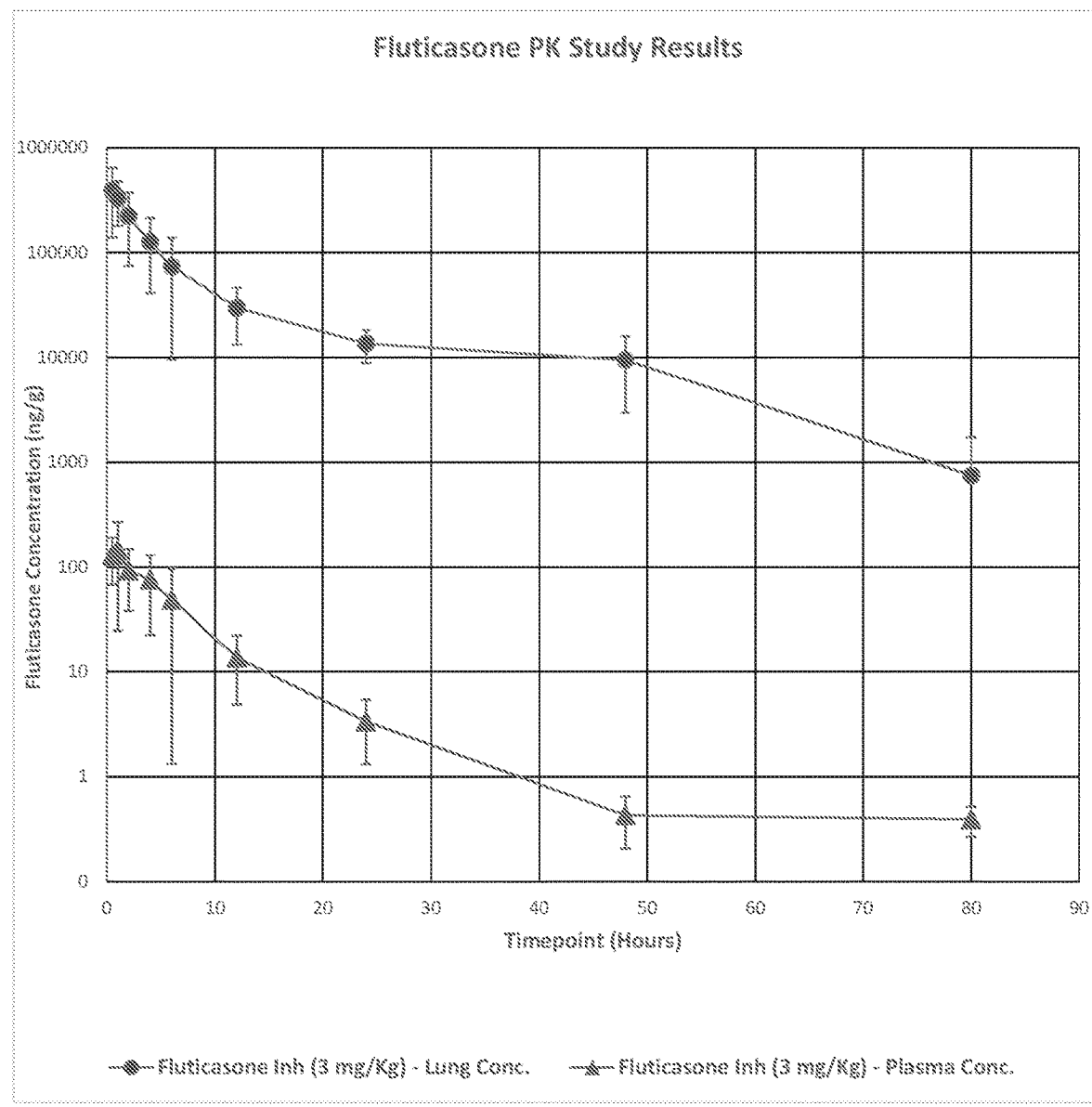
Figure 6:
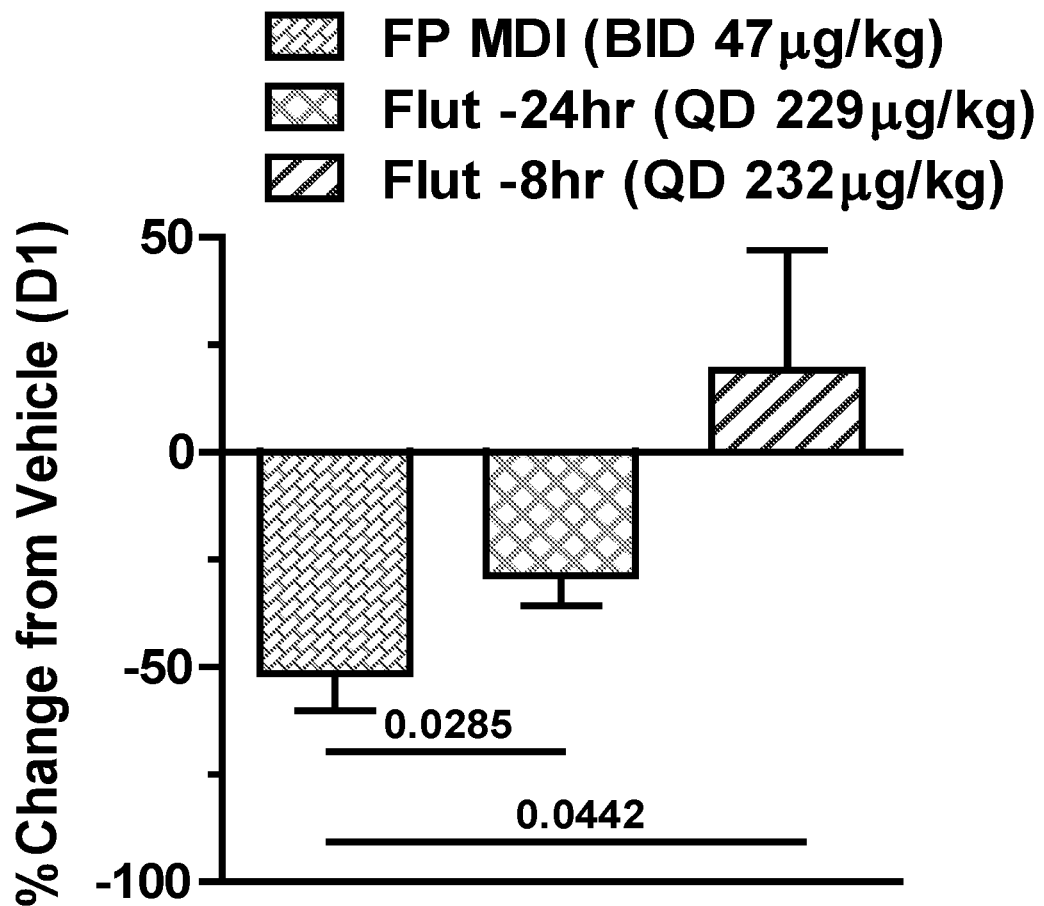
Figure 7:
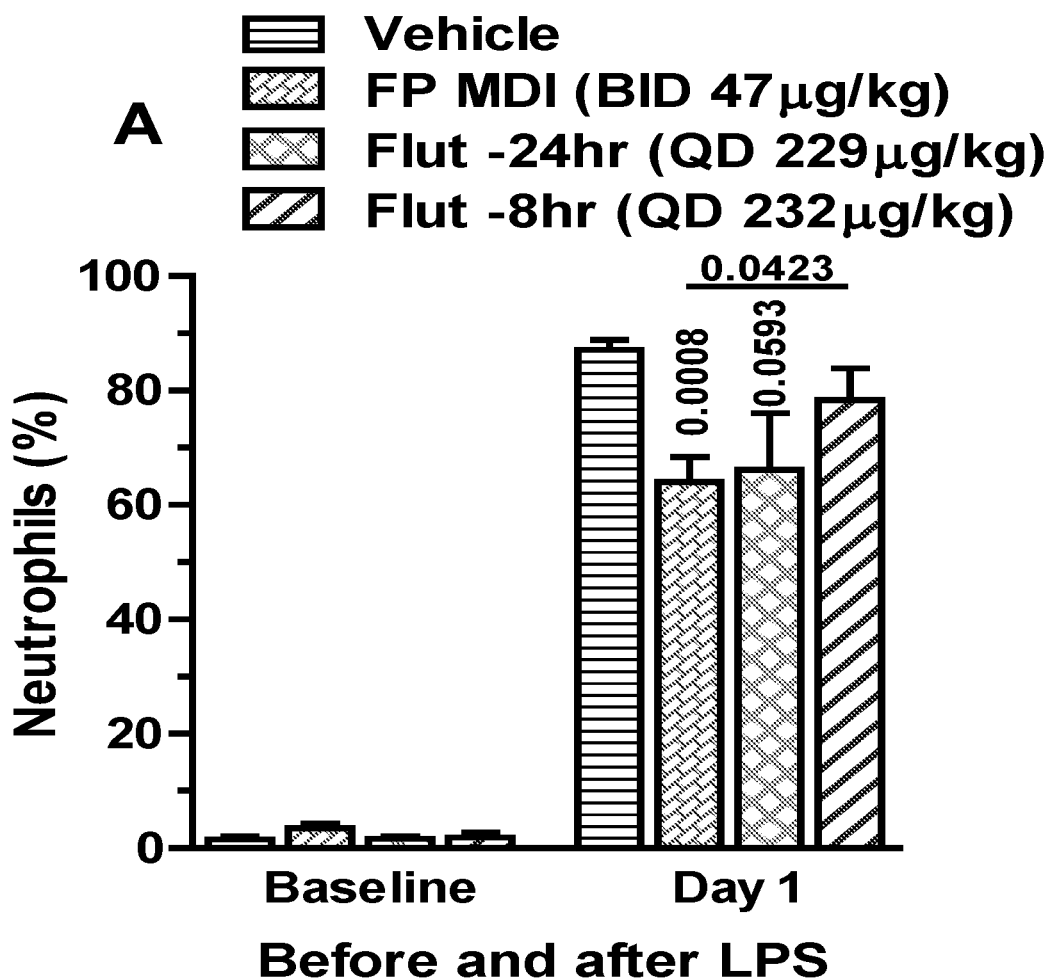
Figure 8:
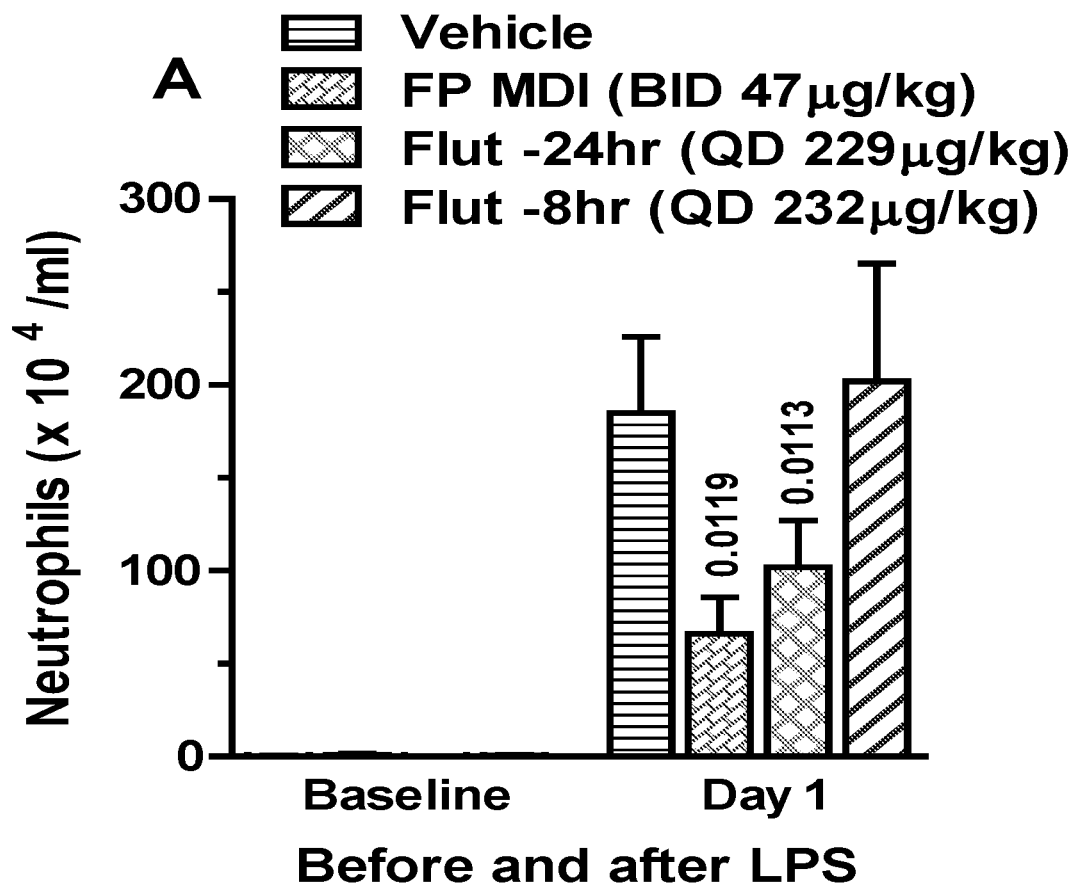
Figure 9:
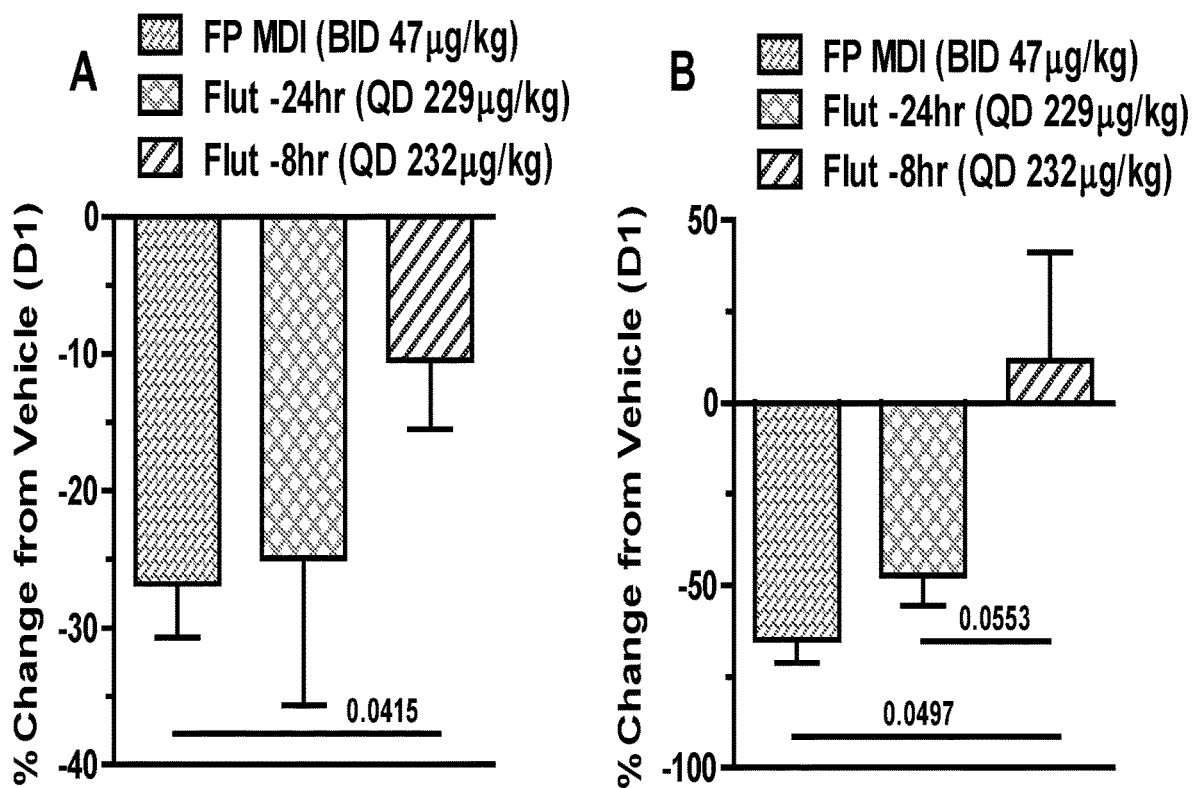
Figure 10:
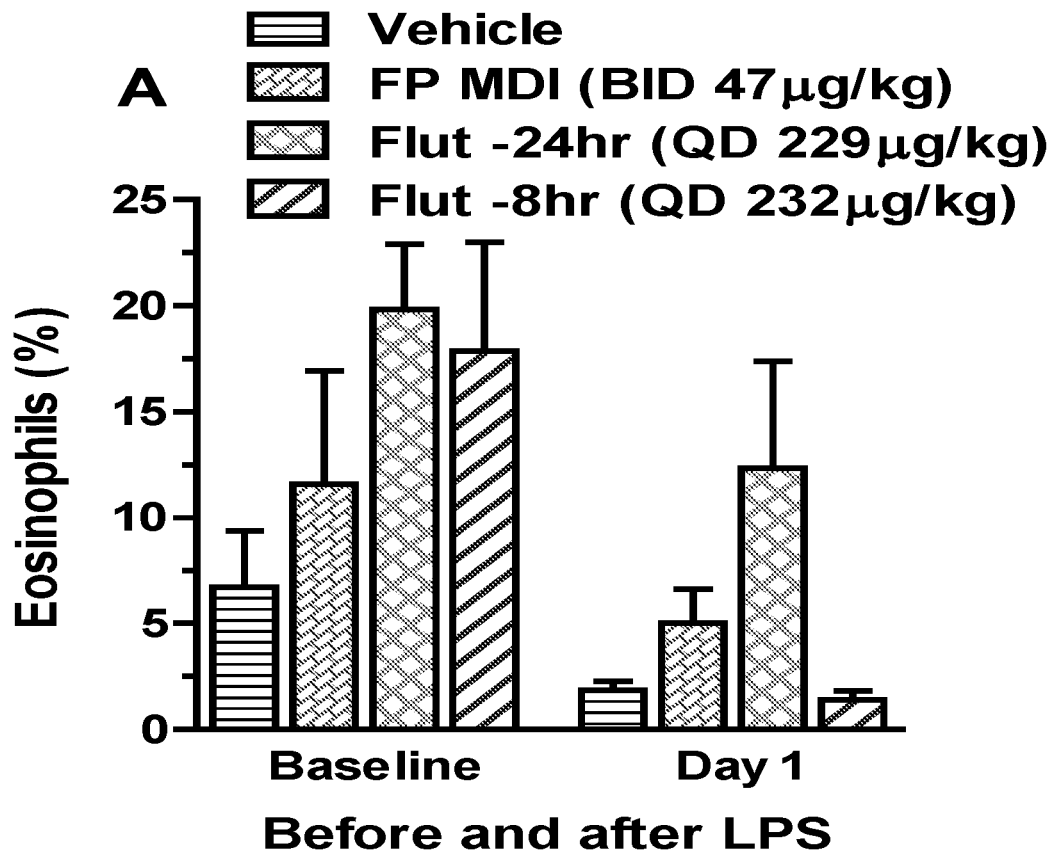
Figure 11:
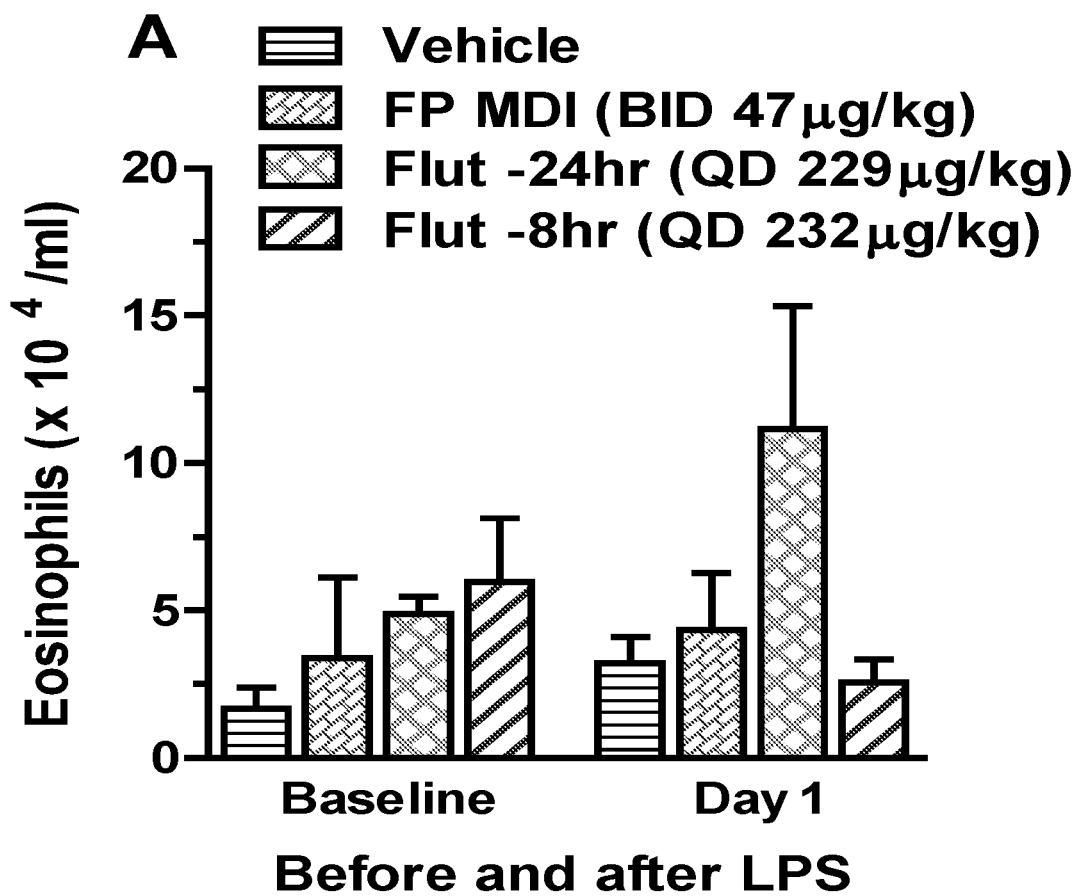
Figure 12:
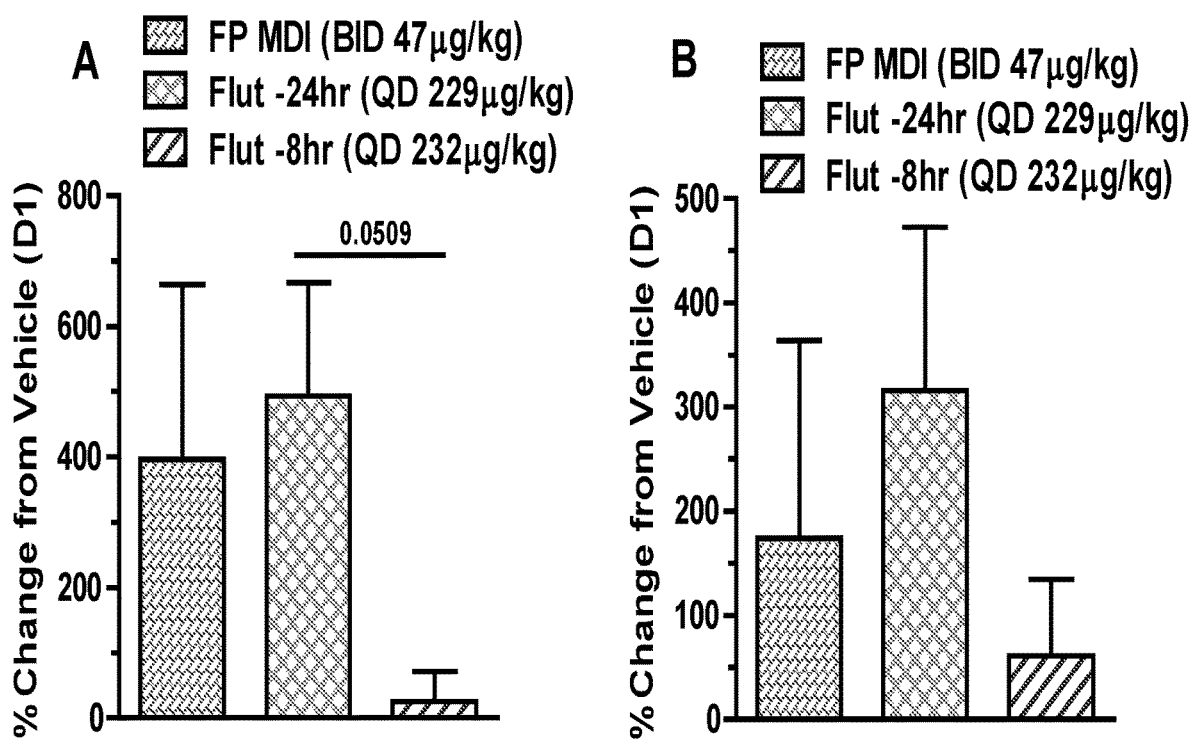
Figure 13:
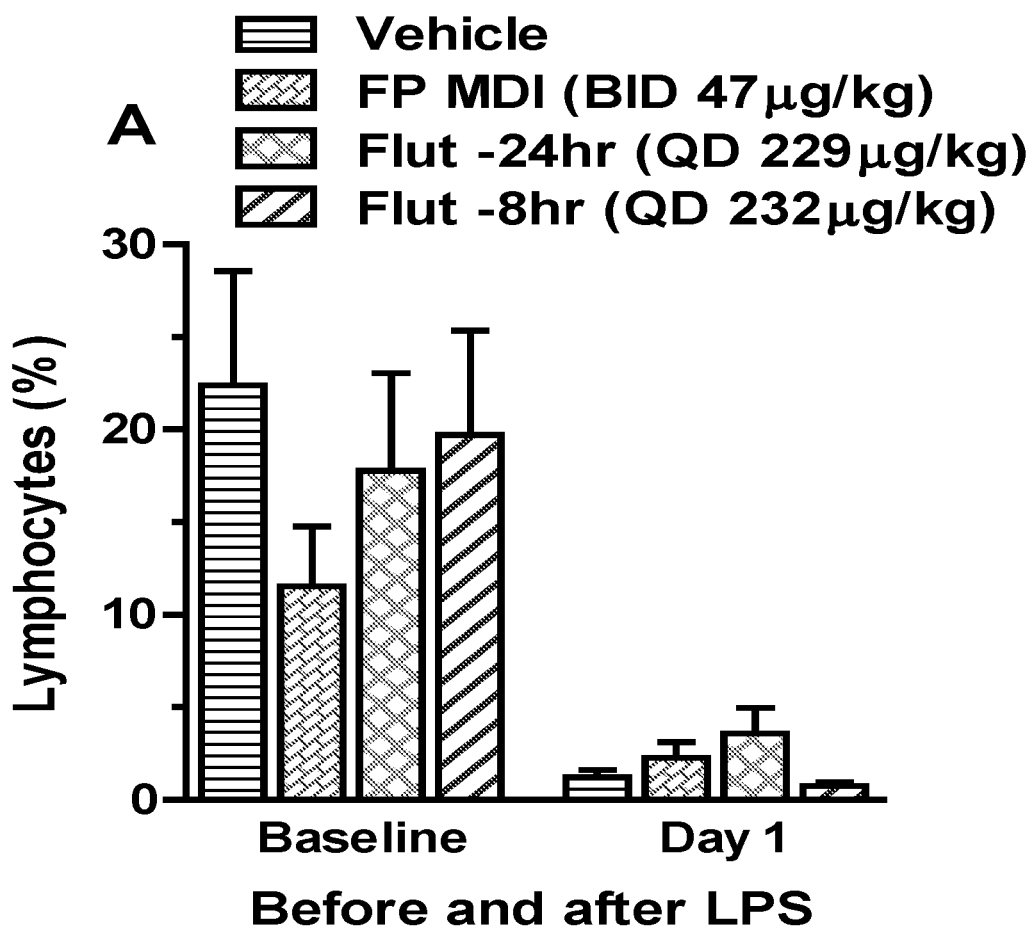
Figure 14:
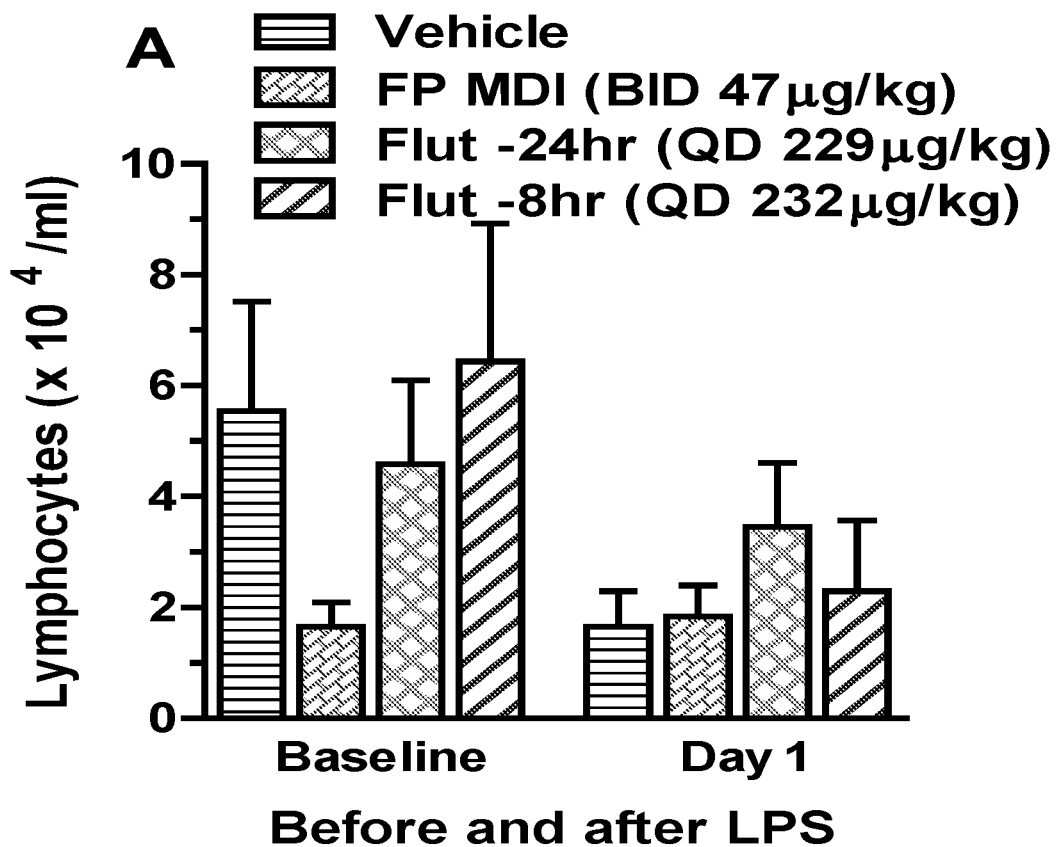
Figure 15:
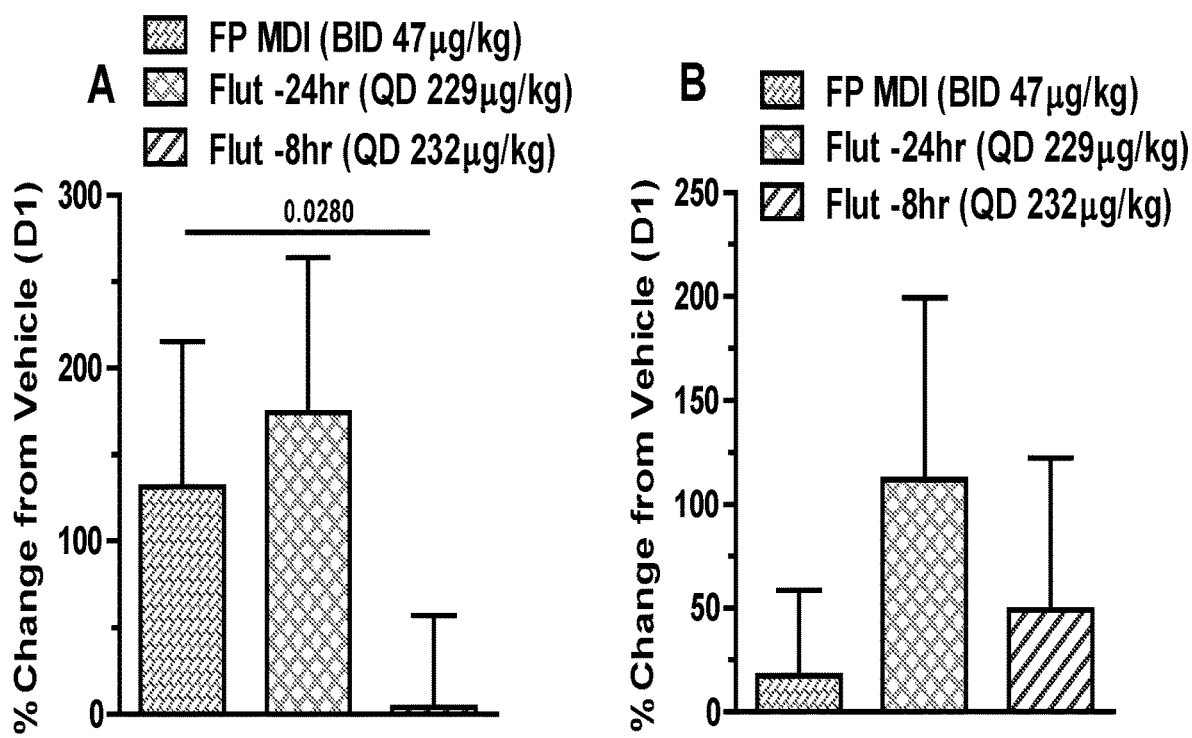
Figure 16:
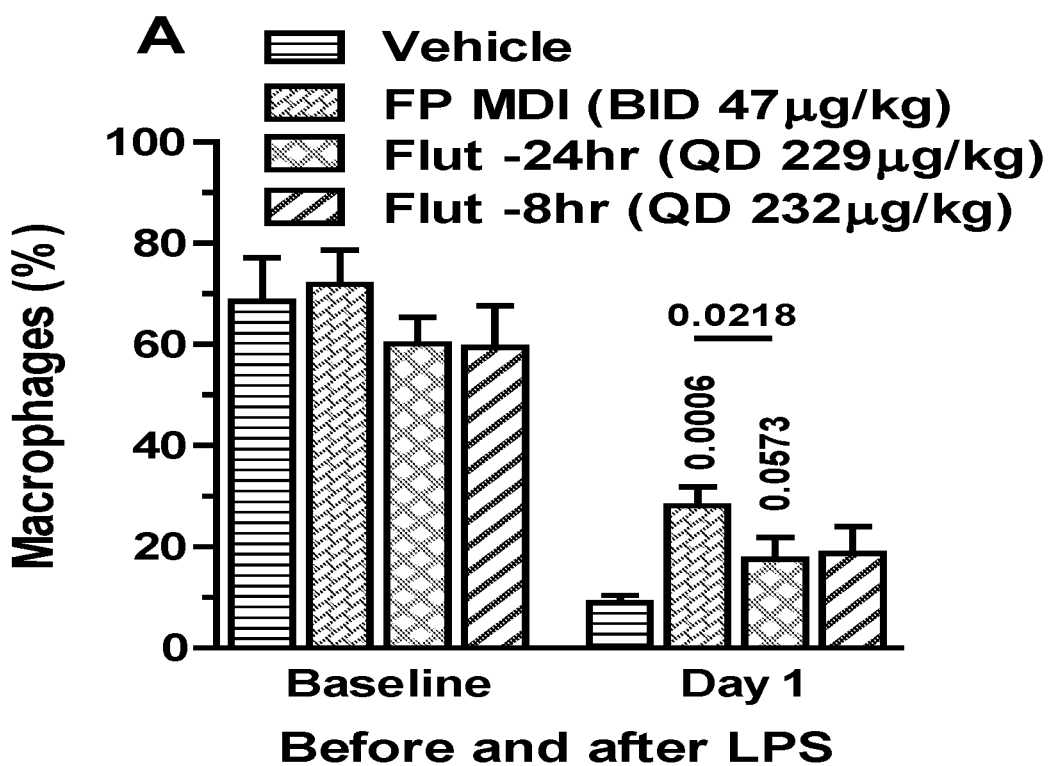
Figure 17:
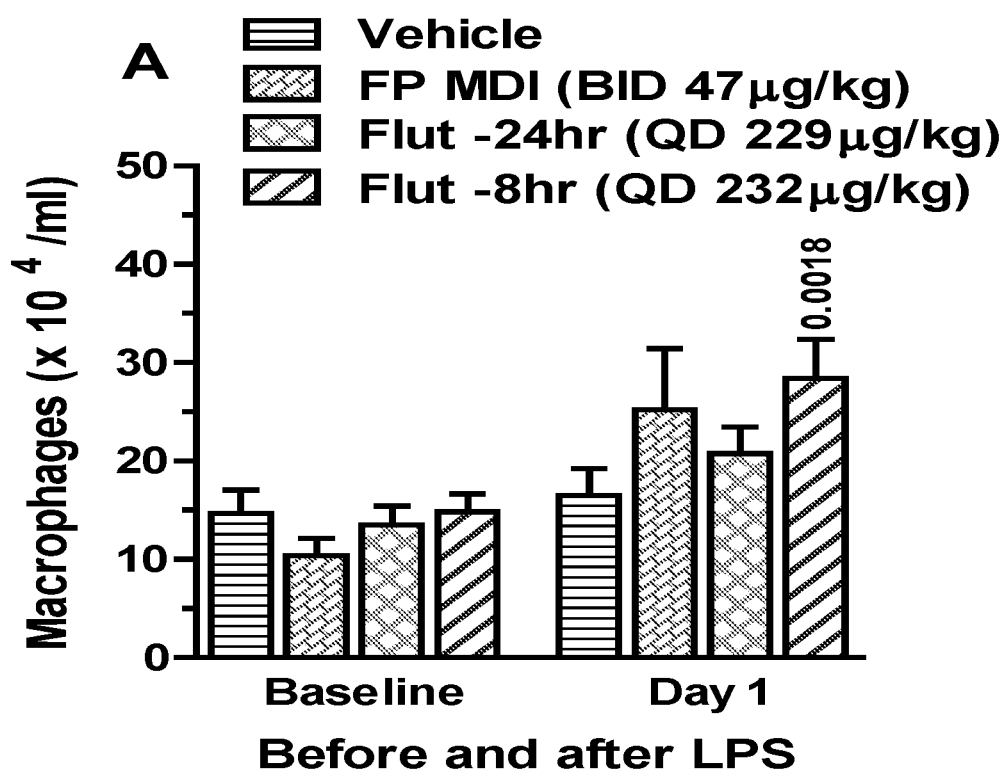
Figure 18:
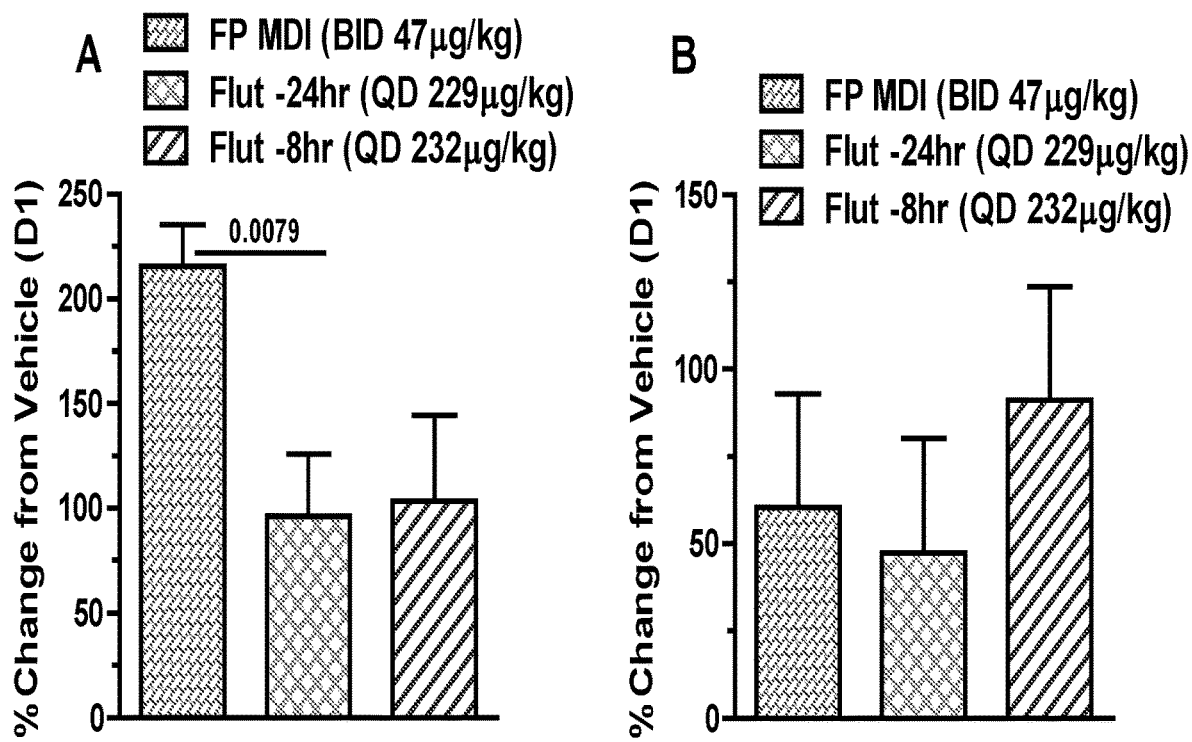
Figure 19:
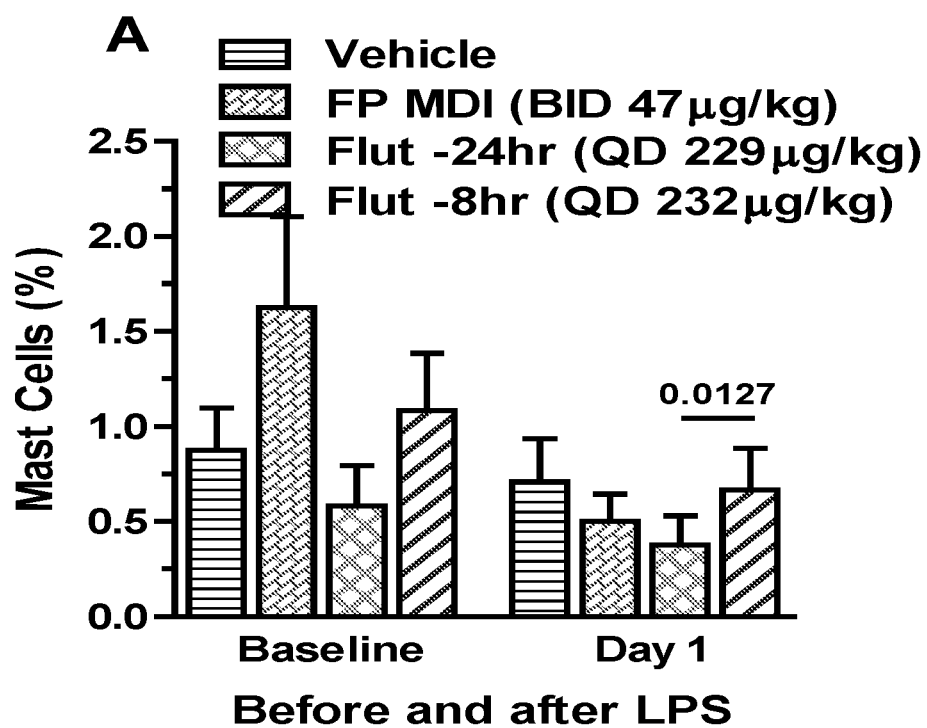
Figure 20:
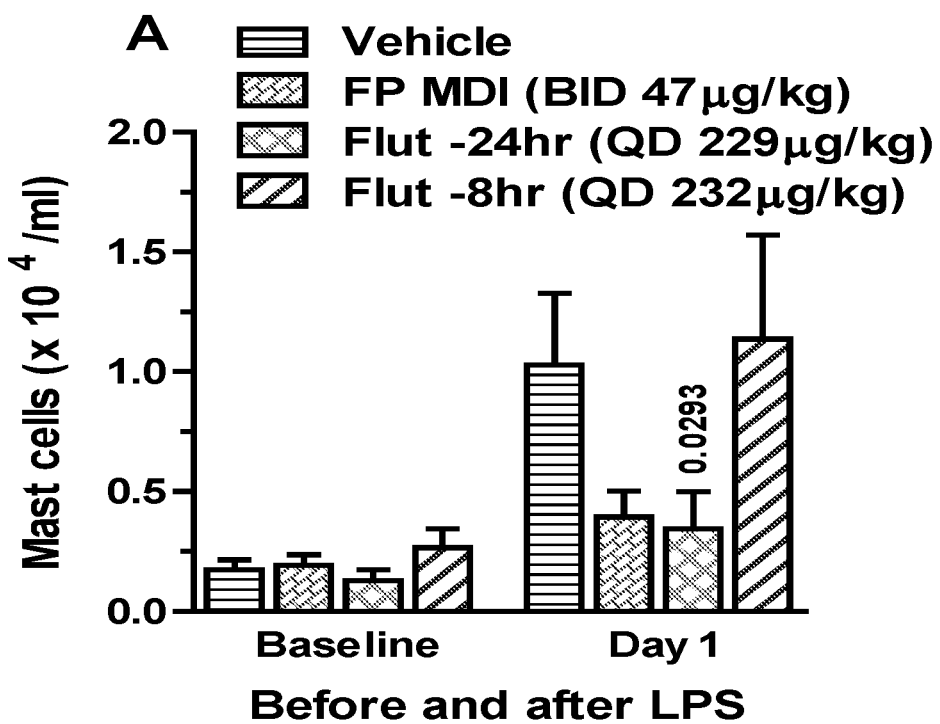
FIG. 20. Number of Mast Cells in BAL. Number of mast cells in BAL collected at baseline (BL) and about 24 hours (D1) after LPS shown as bar graph (A, mean±sem, n=6). FLOVENT® (FP MDI) was given one hour prior and 6 hours post LPS and fluticasone formulation (Flut) either 24 or 8 and vehicle 24 hours prior to LPS. Number of mast cells increased significantly for vehicle treated group from BL to D1. Number of mast cells on D1 were significantly lower after fluticasone formulation given 24 hours before LPS compared to vehicle treatment (Paired t-test).
Figure 21:
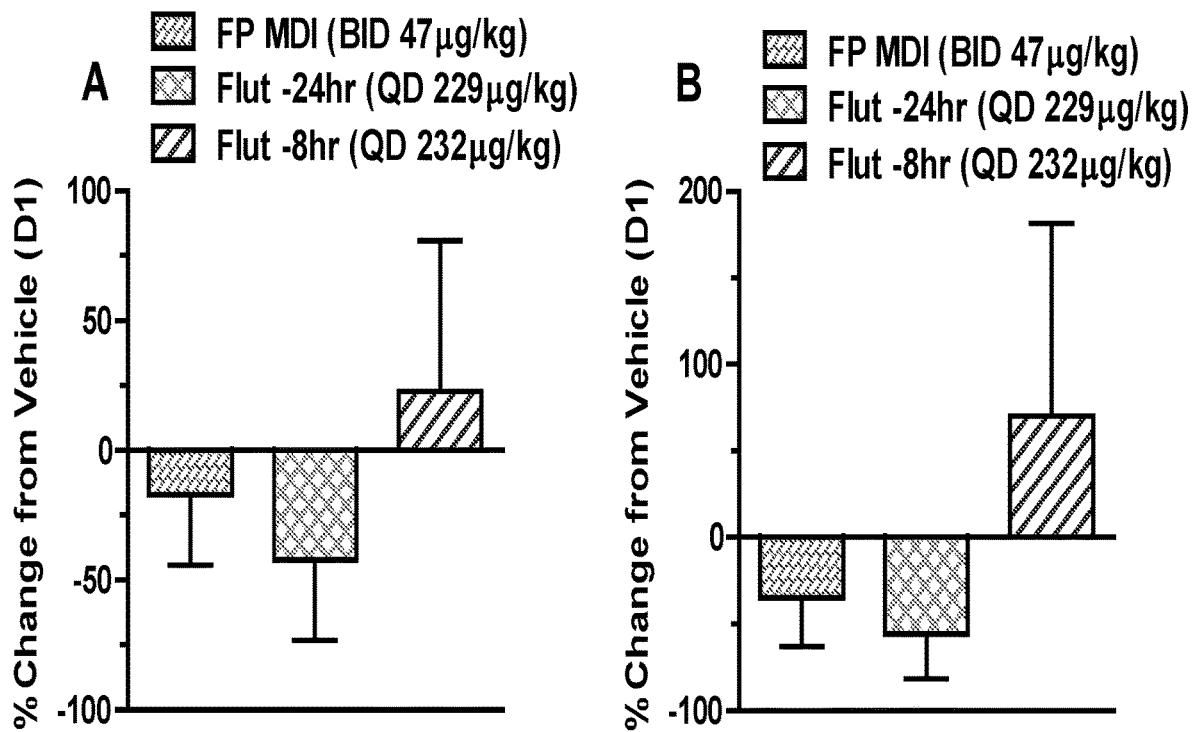
FIG. 21. Change in Mast Cells from Vehicle Response on Day 1. Percent (A) and number (B) of mast cells in BAL as shown in FIG. 19 and FIG. 20 were not different between any of the treatment groups in reference to vehicle treatment (=0%).

Results are summarized in FIG. 5 and demonstrate that quantifiable levels of fluticasone were observed at 80 hours in both lung and plasma tissue, with approximately 1000-fold more fluticasone in the lungs than in the plasma.

3. Pharmacokinetic Dog Study for Processed Fluticasone Particles

Summary

The objective of this study was to evaluate anti-inflammatory properties of fluticasone particles of the disclosure in a dog Lipopolysaccharide (LPS) model. The LPS model causes respiratory inflammation that mimics characteristics of various respiratory diseases. This experiment was designed to provide pharmacodynamic and pharmacokinetic data. The steroid FLOVENT® HFA (hydrofluoroalkane) used for treatment of asthma, COPD (chronic obstructive pulmonary disease), hay fever and other lung diseases was utilized as a positive control to compare the efficacy of this formulation.

FLOVENT® (GlaxoSmithKline—GSK) was delivered by metered-dose inhaler (MDI) and fluticasone propionate particles of the disclosure (also referred to as the "fluticasone formulation") were delivered as a dry powder using insufflator devices and a bolus delivery system (Lovelace Biomedical). The aerosol was characterized for amount delivered and particle size distribution at the terminus of the endotracheal tube. Mass median aerodynamic particle size (MMAD) of the aerosol was 2.46 µm with a geometric standard deviation (GSD) of 1.74 as measured by Aerodynamic Particle Sizer (APS). The specific surface area of the fluticasone propionate particles used in this study was approximately 11.85 m²/g.

Six male Beagle dogs were utilized for a total of 4 experiments separated by at least two weeks. In the first experiment of this study, anesthetized animals received two inhaled treatments of FLOVENT® HFA (20 actuations each, resulting in 47 µg/kg) given 1 hour prior to and 6 hours post LPS challenge. Thereafter, the novel fluticasone formulation was given either 24 (229 µg/kg) or 8 hours (232 µg/kg) prior to LPS to determine effect on lung inflammation. Based on the results of these first three experiments, a proper vehicle experiment was added via amendment and dogs were treated with empty insufflator devices 24 hours prior to LPS challenge to mimic one of the fluticasone treatment scenarios. LPS was freshly prepared on day of use and given by inhalation via PARI LC nebulizer (2 minutes of 0.5 mg/ml). Bronchoalveolar lavages (BAL) were done 3 to 4 days prior to treatment and about 24 hours after LPS challenge to determine level of lung inflammation.

Samples for PK analysis were collected before and after BID treatment with FLOVENT® (pre and at 5, 15, 30, 45 and 60 minute post exposure 1 and pre and at 5, 15, 30, 45, 60, 90, 120, 240 and 1200 minutes post exposure 2). Furthermore, plasma samples were collected before and at 5, 15, 30, 60, 90, 120, 240 minutes post fluticasone formulation and 8 and 12 hours (only for 8 hour pre-treatment) and 24 hours (only for 24 hour pre-treatment), processed within one hour of collection and frozen prior to analysis by liquid chromatography-mass spectrometry (LC/MS). No PK samples were collected during vehicle treatment.

LPS inhalation challenge induced lung inflammation measured about 24 hours thereafter indicated by a statistically significant increase in total cell numbers and neutrophil infiltration in the lung in all treatment groups. As seen in previous studies, BID treatment with FLOVENT® (47 µg/kg) significantly attenuated the LPS-induced lung inflammation. A single treatment with the fluticasone formulation given 24 hours prior to LPS (229 µg/kg) resulted in a similar attenuation of the inflammation indicated by a decrease in total cell numbers and number of neutrophils compared to a BID treatment with FLOVENT®. In contrast, pre-treatment with fluticasone formulation (232 µg/kg) given 8 hours prior to LPS did not alter lung inflammation despite showing a similar PK profile.

Overall, a single pre-treatment with the novel fluticasone formulation shows efficacy similar to FLOVENT® (BID) depending on the time of treatment.

Experimental Details

Methods

Six Beagle dogs served as their own control and were used in a total of 4 experiments separated by at least two weeks of recovery/resting period. The vehicle experiment was added after conclusion of the first three study legs via amendment in order to determine efficacy of these formulations to appropriate control treatment. "TA" refers to the fluticasone formulation.

Study Legs (1) FLOVENT® (BID 47 µg/kg) delivered by inhalation one hour prior and 6 hours post LPS (obtained from Sigma Chemical Company)
(2) TA (QD 229 µg/kg) delivered by inhalation 24 hours prior to LPS
(3) TA (QD 232 µg/kg) delivered by inhalation 8 hours prior to LPS
(4) Vehicle Control delivered by inhalation 24 hours prior to LPS (empty insufflator devices All exposures and bronchoalveolar lavage procedures were done under isoflurane anesthesia. For all study legs, bronchoalveolar lavages (BAL) were done 3 or 4 days prior to treatment and about 24 hours after LPS challenge to determine effect of treatment on LPS induced lung inflammation. For the first experiment, dogs were treated one hour prior to LPS challenge and kept under light anesthesia covered with blankets after the first TA exposure (0 hour) until the LPS challenge was completed (1 hour). They were re-anesthetized for the second exposure 6 hours thereafter (only for leg 1). The fluticasone formulation was either given 24 hours (Leg 2) or 8 hours (Leg 3) prior to LPS. Treatment with the appropriate vehicle control (empty insufflator devices) was only done 24 hours prior to LPS.

Test System

A total of six dogs used in this study (1.8 to 4.1 years of age) were single or dual-housed in indoor/outdoor dog kennel buildings. The environmental conditions (room temperature, humidity, light cycle) were continuously stored in the Rees Environmental Monitoring System SQL database. The temperature was within the required range of 18° C. to 29° C. with a lighting cycle of 12 h on (6 AM to 6 PM) and 12 h off for the duration of all experimental legs.
Dogs received Harlan 2025 certified dog chow (Harlan Teklad, Madison, WI) once a day with unlimited access to water. On experimental days that required anesthesia, food was withheld the night prior to the procedure and dogs were not fed until all experiments were completed and the animals were recovered. In study leg 3, dogs received some treats and/or special food in between treatment (after 2 hour PK sample) and LPS challenge and the normal food was not given until they recovered from second anesthesia for LPS challenge.

Anesthesia

Dogs were anesthetized with isoflurane during exposures and bronchoalveolar lavage procedures (4-5% for induction via face mask, 1 to 2.5% for maintenance), and an appropriate sized endotracheal tube was placed in the trachea. Following exposures and sample collection the anesthesia was discontinued for recovery. Only for study leg 1 (FLOVENT® MDI) animals were kept under light anesthesia during the one hour period between the AM treatment and LPS challenge (1.5 to 2.5% isoflurane) and covered with a blankets to avoid a too rapid drop in body temperature. A pulse oximeter was used to monitor heart rate and saturated oxygen during anesthesia.

LPS Preparation and Exposures

The canine exposure system is designed to expose individual anesthetized animals via an endotracheal (ET) tube. LPS (Sigma, L-7018) aerosol was generated with a PART LC compressed air nebulizer filled with about 3 ml of 0.5 mg/ml solution. The nebulizer was operated at 20 psi, which results in an output of ~4.5 L/min. The nebulizer itself was mounted onto a two-way valve (Rudolph Valve, Hans Rudolph, Inc.; Kansas City, MO) connected to a respirator, Harvard Pump, (Harvard Apparatus; Holliston, MA) operated at ~3.0 L/min. Dogs were mechanically ventilated during the 2 minute exposure (volume ~225 ml; ~18 breaths/minute).

Inhalation Treatment

A bolus delivery system was used to deliver appropriate amount of FLOVENT® and fluticasone formulation using insufflator devices based on individual body weights. Inhalation treatment was done as follows. Apnea was induced in an anesthetized and intubated dog, the pMDI or insufflators were connected to the expansion chamber attached to the endotracheal tube and the aerosol "puffed" into the lungs with positive pressure using an Ambu-bag.

FLOVENT® HFA

Dogs received two inhaled treatments given 1 hour prior to and 6 hours post LPS challenge. FLOVENT® was delivered via metered dose inhaler (MDI) and previous studies showed that 20 actuations of the MDI achieved the target dose of about 50 µg/kg (10 to 12 kg dog) resulting in significant attenuation of the LPS induced lung inflammation. The MDI was disconnected from the chamber and inverted in between each actuation in order to achieve uniform delivery. The MDI was weighed prior and after delivery to determine the net weights and therefore the amount of delivered material.

Fluticasone Propionate (TA) Treatment

Aerosol characterization to determine optional delivery of the fluticasone formulation via insufflator (total amount needed in insufflators) was done prior to the efficacy experiment. The appropriate amount was filled in several insufflators (7 to 9 based on body weight) and the dry powder in each of the insufflators was delivered with three consecutive puffs by simultaneous pushing the Ambu-bag and injecting 3×10 ml of air in the insufflator using a syringe. The insufflator devices were weighed prior and after delivery to determine the net weights and therefore the amount of delivered material. A total of 8 empty insufflator devices were used for the vehicle experiment.

Bronchoalveolar Lavage Procedures

Bronchoalveolar lavages (BAL) were collected 3 days prior to first treatment (baseline) and about 24 hours post LPS exposure. During each BAL session animals were anesthetized with isoflurane, intubated with the appropriate sized endotracheal tube and lavaged with 5×10 ml saline for irrigation in one right and one left lung lobe. Briefly, a fiberoptic bronchoscope was guided past the carina into one side of the lung and wedged into an appropriately sized airway. Subsequently, five 10 ml washes of sterile saline for irrigation were introduced through the bronchoscope in one side of the lung and aspirated immediately. The volume of the recovered lavage fluid was recorded. The procedure was repeated in the contralateral side and lavage samples were kept on ice until processing. After centrifugation of the samples at about 1600 rpm and 4° C. for 10 min supernatant was separated from the cells and discarded. Cells were washed once with PBS, suspended in 5 ml of RPMI+10% FBS and total cells counted using an automated cell counter (Nexelcom Cellometer). A total of 50,000 cells per slide (in duplicates for right and left sample) were used to prepare cytospins and the remaining cells were discarded. The cells on the slides were fixed and stained using a modified Wright-Giemsa stain. Differential counts on at least 200 nucleated cells per sample were conducted using morphological criteria to classify cells into neutrophils, macrophages, lymphocytes, mast cells and eosinophils and presented as average of right and left expressed as % cells and as number of cells normalized to recovery volume.

Blood Collection

Blood samples for pharmacokinetic endpoints (~2 ml in $K_2$EDTA for each time point) were collected from the jugular vein directly into the vacutainer or using a syringe. Some of the time points (e.g. between TA treatment and LPS exposure in leg 1) were done during anesthesia and therefore collected from a venous catheter (cephalic or saphenous) placed during induction of anesthesia. A total of 16 blood samples were collected before and after FLOVENT® MDI (Pre, 5, 15, 30, 45, 60 minutes post AM treatment and pre, 5, 15, 30, 45, 60, 90, minutes, 2, 4, 24 hours post PM treatment). Similarly, a total of 10 or 11 samples were collected before and after treatment with the novel fluticasone formulation given 24 and 8 hours prior to LPS (pre, 5, 10, 30, 45, 60, 90 minutes, 2, 4, 24 hours and pre, 5, 10, 30, 45, 60, 90 minutes, 2, 4, 8 and 12 hours, respectively). Blood samples were kept on ice until processing within less than 1 hour of collection. After centrifugation (2800 rpm, 4° C., 10 min) two aliquots were stored at −60 to −80° C. until analysis.

Statistical Analysis

Paired T-test was used to test statistical significance on changes in cell differentials after LPS challenge and TA treatment to determine level of efficacy compared to vehicle treatment. A value of p<0.05 was considered significant (GraphPad Software, San Diego, CA).

Results

Body Weights and Animal Observations

None of the treatments induced any side effects and animals recovered from the experiments within less than one hour. No change in body weights were seen during the duration of the study Exposure Results The average exposure levels and duration of dosing are shown in Table 3.

TABLE 3

Exposure Details and Results

| | Treatment | Delivery Device | Time in min (mean ± sem) | Dose in µg/kg (mean ± sem) |
|---|---|---|---|---|
| Leg 1 | FLOVENT® MDI | MDI (20 actuations) | 1.6 ± 0.1 (AM) 1.4 ± 0.1 (PM) | 47.3 ± 2.6 |
| Leg 2 | Fluticasone TA (−24 hrs) | 8 to 9 filled insufflators | 3.0 ± 0.2 | 229.0 ± 4.6 |
| Leg 3 | Fluticasone TA (−8 hrs) | 7 to 8 filled insufflators | 2.5 ± 0.1 | 231.7 ± 2.2 |
| Leg 4 | Vehicle (−24 hrs) | 8 empty insufflators | 1.7 ± 0.1 | N/A |

Deposition calculated based on in vitro tests done during aerosol characterization—exposure time calculated based on actual body weight of dogs during each leg.

The appropriate delivered doses were calculated based on aerosol characterization and actual body weights obtained on day of dosing. Therefore, an average dose of 47 µg/kg of FLOVENT® was delivered BID compared to a single dose of 229 and 232 µg/kg for Fluticasone formulation given 24 and 8 hours prior to LPS challenge, respectively. Dosing time for FLOVENT® was less than 2 minutes compared to about 2.5 to 3 minutes for the fluticasone formulation by utilizing 7 to 9 insufflators filled with the appropriate amount of test article. Accordingly, a total of 8 empty insufflators were used for vehicle treatment given 24 hours prior to LPS and dosing lasted less than 2 minutes.

Total Cell Numbers and Cell Differentials in Bronchoalveolar Lavage

LPS inhalation challenge induced a statistically significant lung inflammation in vehicle treated group indicated by an increase in total cell number as well as percent and number of neutrophils from baseline to day 1 ($22.5\pm2.9\times10^4$ to $207.3\pm43.4\times10^4$, 1.5±0.5% to 87.2±1.7% and $0.4\pm0.2\times10^4$ to $184.9\pm40.9\times10^4$, respectively) as determined by Paired t-test. Due to the increase in total cell numbers, the lymphocyte and macrophage numbers showed only minor changes from baseline to day 1 despite the decrease in percent of lymphocytes (22.4±6.2% to 1.3±0.4%) and macrophages (68.5±8.7% to 9.1±1.4%). Some of the dogs experienced some higher eosinophil counts at baseline which seemed to be partially attenuated after LPS exposure and treatment, but only small numbers of mast cells were present before and after LPS challenge.

The increase in total cell numbers as well as neutrophil percent and numbers seen in vehicle group 24 hours after LPS challenge was significantly attenuated after treatment with FLOVENT® and fluticasone formulation given 24 hours prior to LPS, but not for fluticasone formulation given 8 hours pre LPS. Minor changes in the other cell populations are partially caused by compensation of the change in neutrophils as the main player for LPS-induced lung inflammation.

The percent change from vehicle on day 1 was calculated for each treatment group (Table 4). Treatment with FLOVENT® and fluticasone formulation given 24 hours prior to LPS significantly attenuated total cell numbers as well as percent and number of neutrophils (−64.8±8.6 and −32.6±7.0, −23.5±4.0 and −24.7±10.7, 73.2±6.4 and −49.6±8.2, respectively), but only minor changes were seen for fluticasone formulation given 8 hours prior to LPS. In addition, FLOVENT® was more slightly efficacious in attenuating the LPS-induced lung inflammation compared to the 24 hour dosing scenario with being statistically significant for total cell numbers and borderline significant for neutrophil numbers (data not shown).

TABLE 4

Percent Change from Vehicle Response on Day 1

| | FLOVENT® MDI (BID 47 µg/kg) | Fluticasone −24 hrs (QD 229 µg/kg) | Fluticasone −8 hrs (QD 232 µg/kg) |
|---|---|---|---|
| Total Cell Number | −64.8 ± 8.6 | −32.6 ± 7.0 | +25.2 ± 27.9 |
| Neutrophils (%) | −23.5 ± 4.0 | −24.7 ± 10.7 | −3.7 ± 5.1 |
| Eosinophils (%) | +238.5 ± 267.4 | +484.6 ± 175.0 | −7.4 ± 46.2 |
| Lymphocytes (%) | +156.7 ± 83.7 | +232.2 ± 89.3 | +38.3 ± 52.9 |
| Macrophages (%) | +224.1 ± 19.6 | +113.5 ± 29.9 | 61.4 ± 41.4 |
| Mast Cells (%) | −6.7 ± 27.2 | −6.7 ± 30.9 | +73.3 ± 58.0 |
| Neutrophils (#) | −73.2 ± 6.4 | −49.6 ± 8.2 | +21.6 ± 29.5 |
| Eosinophils (#) | +15.7 ± 190.2 | +287.1 ± 157.4 | 4.9 ± 72.7 |
| Lymphocytes (#) | −11.1 ± 41.0 | +109.0 ± 87.1 | +80.5 ± 73.3 |
| Macrophages | +21.0 ± 32.7 | +44.9 ± 32.8 | +92.4 ± 32.3 |

TABLE 4-continued

Percent Change from Vehicle Response on Day 1

| | FLOVENT ® MDI (BID 47 μg/kg) | Fluticasone -24 hrs (QD 229 μg/kg) | Fluticasone -8 hrs (QD 232 μg/kg) |
|---|---|---|---|
| (#) Mast Cells (#) | -52.9 ± 27.8 | -29.4 ± 26.0 | +164.7 ± 110.6 |

FIGS. 6-21 detail results for specific cell populations.

Pharmacokinetic Results

Figure 22:
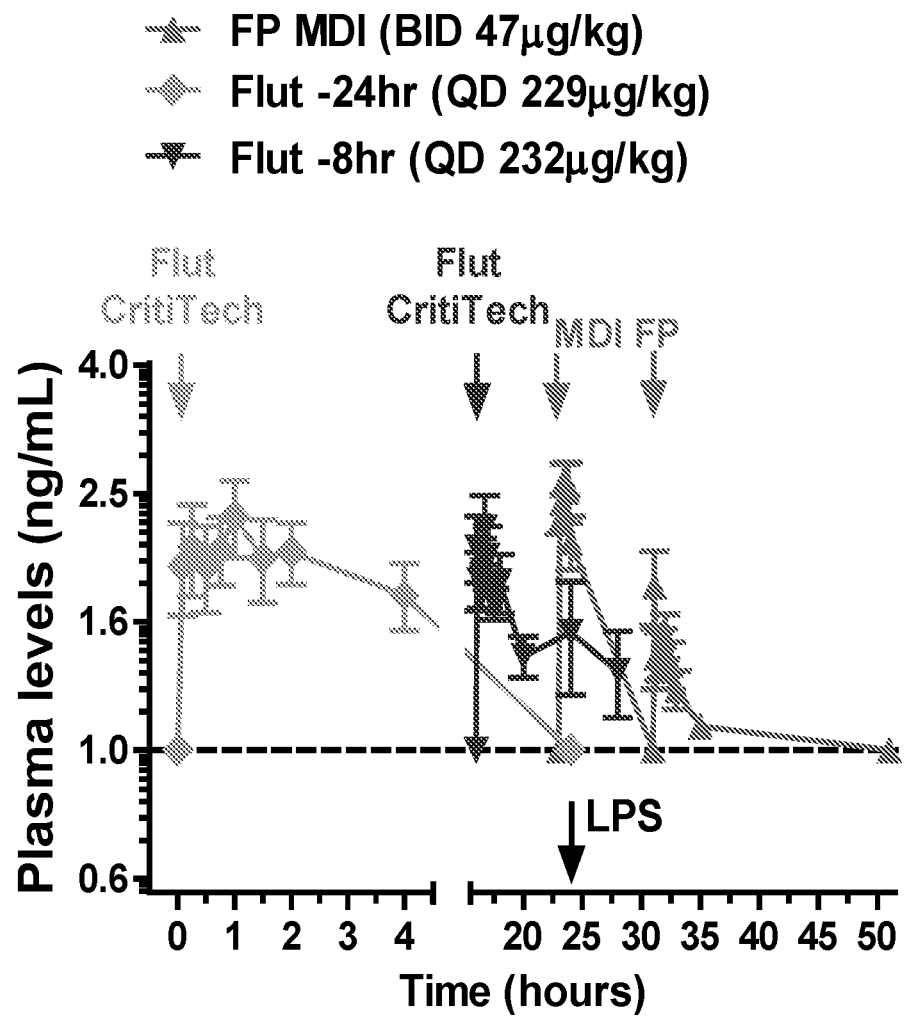
FIG. 22. Plasma Concentration-Time Curves for all Treatments. Plasma concentration-time data for each treatment group expressed as mean±sem (n=6). Peak plasma concentrations were similar in all treatment groups and were reached within 1 minute post treatment with similar peak concentrations of about 2 to 3 ng/ml. The dashed line indicates the detection limit of the assay.

Average plasma concentration-time curve for all treatment groups is shown in FIG. 22. Average results (n=5 or 6) for non-compartmental analysis using WinNonlin [mean±std (% CV)] are summarized in Table 5. PK data for one dog in each of the fluticasone formulation groups was eliminated from the average results in Table 5 due to missing values and therefore no results in analysis could be obtained. Similar maximum plasma concentrations ranging in average from 1.9 to 2.8 ng/ml were reached within less than 1 minute after treatment with FLOVENT® and fluticasone formulation independent from treatment scenario, indicating a similar systemic profile for both formulations. The half-life for both formulations was between 9 and 36 minutes and more variable between dogs and did not result in statistical significance. The area under the curve normalized to the dose was slightly lower in the fluticasone formulation compared to FLOVENT®, especially when treatment was done 24 hours prior to LPS.

given 24 hours prior to LPS (229 μg/kg) attenuated most of the inflammation (total cell numbers, percent lymphocytes, and macrophages). Pre-treatment with fluticasone formulation (232 μg/kg) given 8 hours prior to LPS did not alter lung inflammation.

In terms of PK profile all formulations showed similar $C_{max}$ and rapid $T_{max}$ and systemic exposure. Interestingly the systemic levels of fluticasone are similar with the 24 hr pre-treatment as they are with the second dose of FLOVENT® HFA (AUC of 7.7 and 10.5 hr*ng/mL, respectively), suggesting retention of Fluticasone in the lungs from the novel fluticasone formulation.

Overall, a single pre-treatment with the novel fluticasone formulation shows efficacy similar to FLOVENT® (BID) depending on the time of treatment.

4. Production of Nintedanib Particles Using SCP

A drug solution of nintedanib in methanol having a concentration of 30 mg/mL was prepared. A Lennox with variable diameters (50 μm, 75 μm, or 100 μm) and a sonic probe (Qsonica, model number Q700) were positioned in the crystallization chamber approximately 5 mm, 10 mm, 15 mm, or 20 mm apart. A stainless steel mesh filter with approximately 20 nm holes was attached to the crystallization chamber to collect the precipitated nintedanib nanoparticles. The supercritical carbon dioxide was placed in the crystallization chamber of the manufacturing equipment and brought to approximately 1200 psi at about 38° C. and a flow rate of 65 standard liter per minute (slpm). The sonic probe was adjusted to 20% (140 watts), 40% (280 watts), 60% (420 watts), or 80% (560 watts) of total output power at a

TABLE 5

Average Results for non-compartmental Analysis

| Treatment | | Cmax ng/mL | Tmax min | T½ min | AUClast hr*ng/ mL | AUClast/ dose hr*kg*ng/ mL*μg |
|---|---|---|---|---|---|---|
| FLOVENT ® MDI | -1 hr | 2.8 ± 0.5 (17) | 0.5 ± 0.2 (47) | 8.1 ± 3.6 (44) | 18.4 ± 5.0 (27) | 0.6 ± 0.1 (18) |
| (BID) | +6 hr | 1.9 ± 0.5 (28) | 7.4 ± 0.5 (6) | 8.4 ± 3.2 (38) | 10.5 ± 4.0 (38) | 0.5 ± 0.1 (18) |
| Flut | -24 hr | 2.6 ± 0.8 (29) | 0.7 ± 0.4 (59) | 12.0 ± 7.1 (59) | 7.7 ± 2.4 (31) | 0.2 ± 0.1 (50) |
| Flut | -8 hr | 2.8 ± 0.5 (17) | 0.6 ± 0.4 (69) | 36.3 ± 43.2 (119) | 15.4 ± 3.2 (21) | 0.4 ± 0.4 (104) |

Note:
PM treatment for FLOVENT ® occurred 7 hours post AM treatment and therefore resulting in Tmax of 7.4 minutes (= 0.4 minutes post exposure)

Discussion

The hypothesis of this work was that the novel fluticasone formulation would enable a reduction in the number of doses required in a canine model of acute inflammation. The two end points assessed were local inflammation in BALF and systemic pharmacokinetics.

LPS inhalation challenge induced lung inflammation measured about 24 hours thereafter indicated by a statistically significant increase in total cell numbers and neutrophil infiltration in the lung in all treatment groups. As seen in previous studies, BID treatment with FLOVENT® (47 μg/kg) significantly attenuated the LPS-induced lung inflammation, as measured by total cell numbers, neutrophils, eosinophils, lymphocytes, macrophages and mast cells in BALF. A single treatment with the fluticasone formulation frequency of 20 kHz. The methanol solution containing the nintedanib was pumped through the nozzle at a flow rate of 2 mL/minute for approximately 8 min. Drug crystallization occurred in the vessel and during this period the system pressure, temperature, and flow rate were kept constant. Once the desired amount of drug solution was introduced into the system, the solution inlet valve was closed and pure solvent (3-5 mL) was introduced through the nozzle in order to rinse the nozzle. $CO_2$ was continually pumped through the system for about 30 minutes to flush all remaining solvent and dry the system. The sonication was then stopped, and the drug particles were collected from the system vessel and oven dried for 20 hours to remove all residual solvent.

Figure 3A:
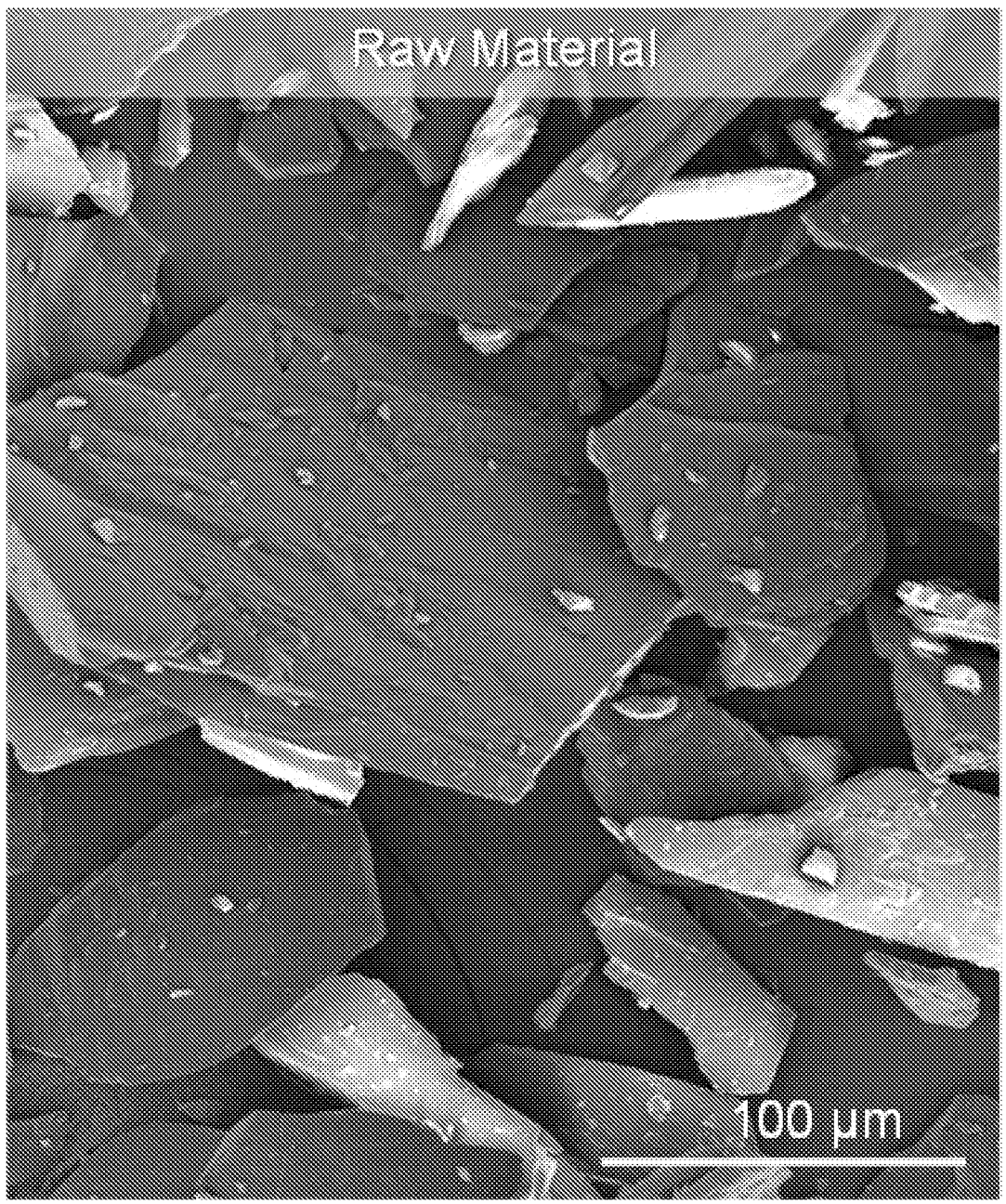
FIG. 3A is an electron micrograph of ra hours post LPS and fluticasone formulation (Flut) either 24 or 8 and vehicle 24 hours prior to LPS. Minor changes in mast cells were seen from BL to D1. There was a statistically significant difference in percent of mast cells on D1 between both of the fluticasone treatment groups (Paired t-test).
Figure 3B:
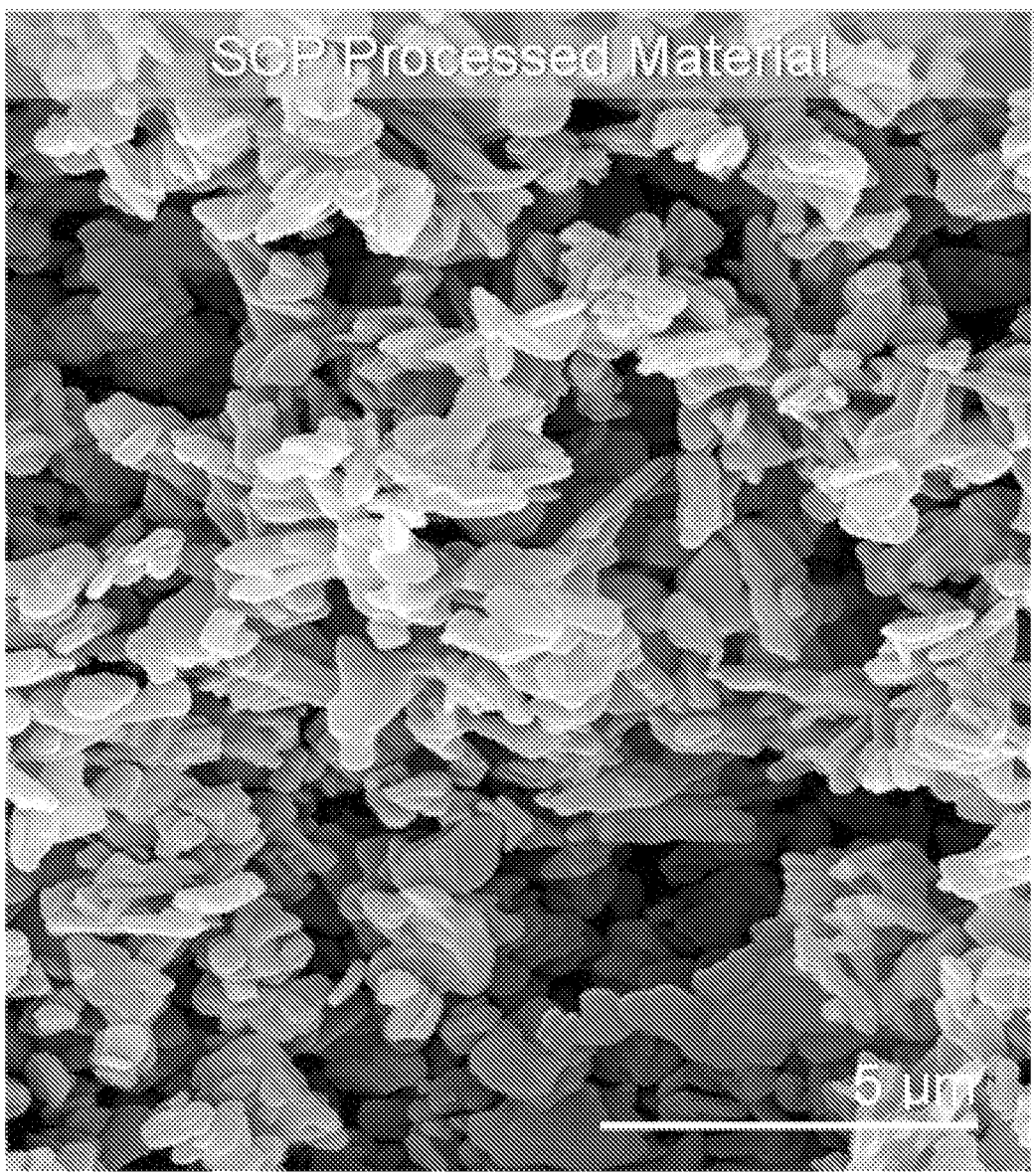

Nintedanib nanoparticles produced had the physical characteristics shown in Table 6, and representative images of the processed nintedanib are shown in FIG. 3B:

TABLE 6

| Characteristic | Raw | SCP | % Change |
|---|---|---|---|
| Dv10 μm | 10.5 | 0.99 | −91% |
| Dv50 μm | 36.8 | 2.36 | −94% |
| Dv90 μm | 70.2 | 4.70 | −93% |
| SSA ($m^2/g$) | 4.11 | 9.94-20.14 | +389% |

Figure 4A:
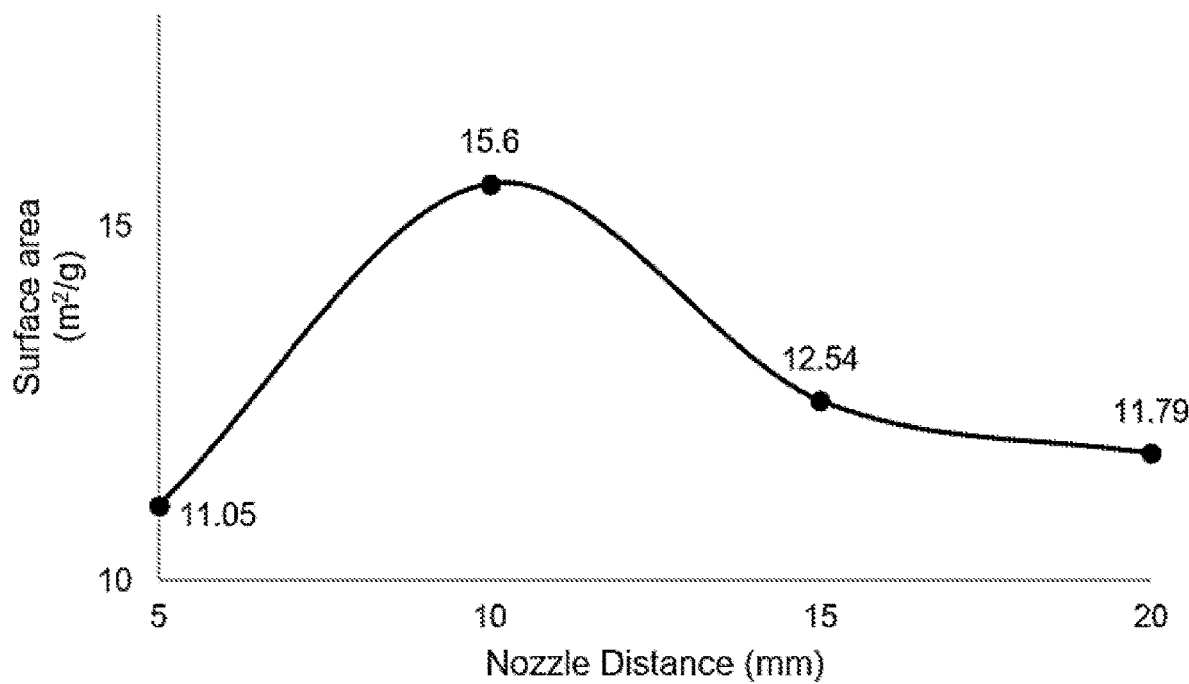
Figure 4B:
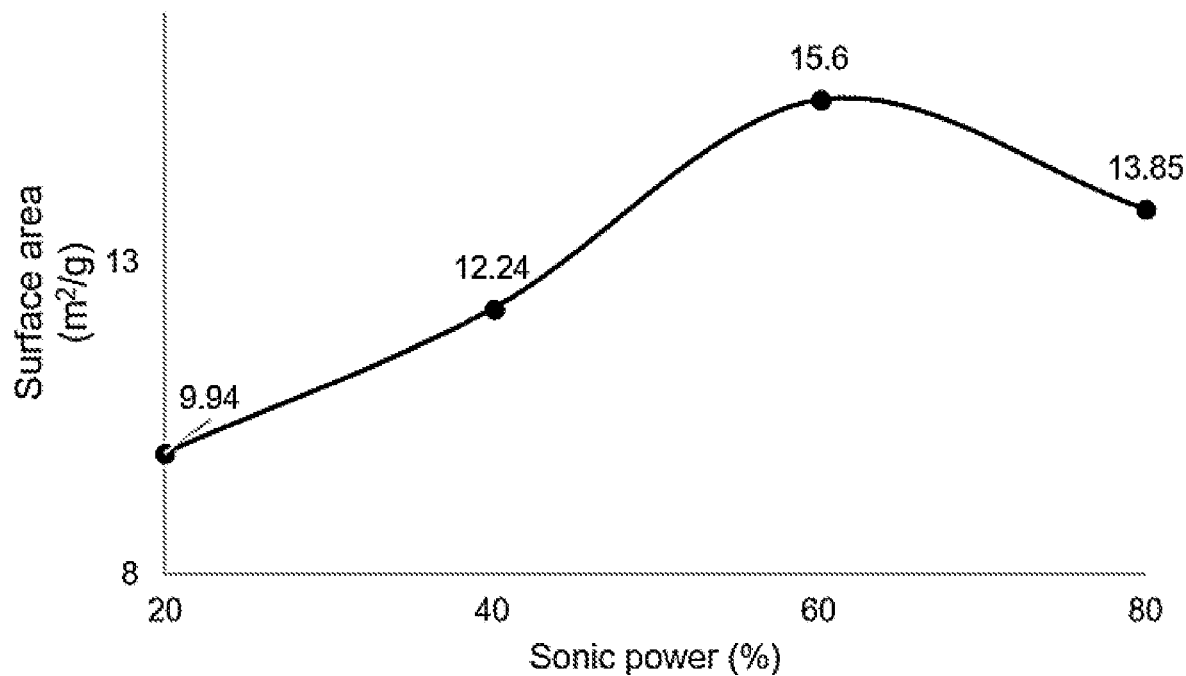
Figure 4C:
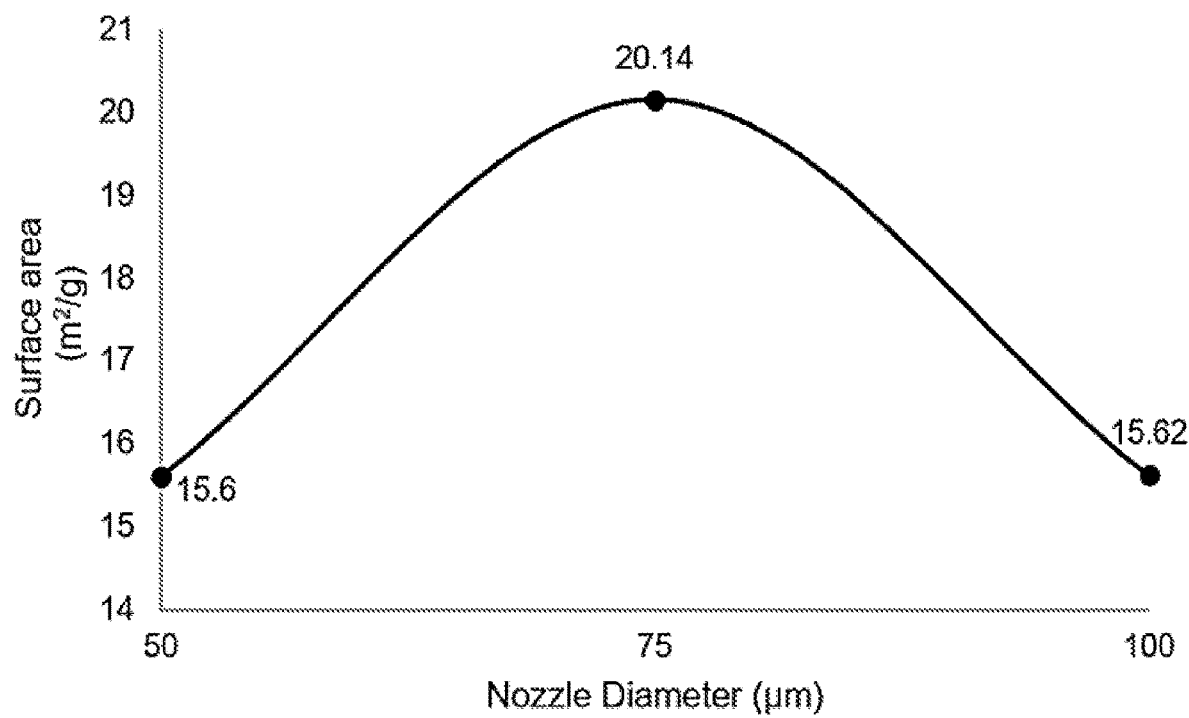

FIGS. 4A-4C are graphs showing the effect on specific surface are of the particles based on nozzle distance from the sonic probe, sonic power, and nozzle diameter, respectively.

We claim:

1. A composition comprising nintedanib particles, wherein the nintedanib particles are at least 99% nintedanib by weight, or a pharmaceutically acceptable salt thereof, wherein the nintedanib particles have a specific surface area (SSA) of between 9 $m^2/g$ and about 20.14 $m^2/g$, wherein the nintedanib particles are not bound to or conjugated to any other substance, and wherein the nintedanib particles have a volume-mean particle size between about 0.5 μm and about 5.0 μm.

2. The composition of claim 1, wherein the nintedanib comprises nintedanib esylate.

3. The composition of claim 1, wherein the composition is present in a suspension that further comprises a pharmaceutically acceptable aqueous carrier.

4. The composition of claim 1, wherein the composition is a dry powder for inhalation.

5. The composition of claim 1, wherein the nintedanib particles have a specific surface area (SSA) of between 9.94 $m^2/g$ and 20.14 $m^2/g$.

6. The composition of claim 1, wherein the nintedanib particles have a specific surface area between 11.05 $m^2/g$ and about 20.14 $m^2/g$.

7. The composition of claim 1, wherein the nintedanib particles are aerosolized and aerosol droplets of the nintedanib particles have a MMAD of between about 0.5 μm to about 6 μm diameter.

8. The composition of claim 6, wherein the nintedanib particles are aerosolized and aerosol droplets of the nintedanib particles have a MMAD of between about 0.5 μm to about 6 μm diameter.

* * * * *